(12) United States Patent
Howell et al.

(10) Patent No.: US 8,112,293 B2
(45) Date of Patent: Feb. 7, 2012

(54) MEDICAL MONITORING SYSTEM

(75) Inventors: Thomas A. Howell, Palo Alto, CA (US);
Angeline Hadiwidjaja, Los Altos, CA (US); C. Douglass Thomas, Campbell, CA (US); Peter P. Tong, Mountain View, CA (US)

(73) Assignee: IpVenture, Inc, Los Altos, CA (US)

( * ) Notice: Subject to any disclaimer, the term of this patent is extended or adjusted under 35 U.S.C. 154(b) by 1297 days.

(21) Appl. No.: 11/725,360

(22) Filed: Mar. 17, 2007

(65) Prior Publication Data

US 2007/0225578 A1    Sep. 27, 2007

Related U.S. Application Data

(60) Provisional application No. 60/785,825, filed on Mar. 24, 2006, provisional application No. 60/880,308, filed on Jan. 12, 2007.

(51) Int. Cl.
*G06Q 50/00*    (2006.01)
(52) U.S. Cl. .................... 705/3; 705/2; 600/300
(58) Field of Classification Search .............. 705/2–3; 600/300
See application file for complete search history.

(56) References Cited

U.S. PATENT DOCUMENTS

| | | | |
|---|---|---|---|
| 4,835,372 A | 5/1989 | Gombrich et al. | |
| 4,860,753 A | 8/1989 | Amerena | |
| 4,883,063 A | 11/1989 | Bernard et al. | |
| 4,931,046 A | 6/1990 | Newman | |
| 4,934,998 A | 6/1990 | Thomas, Jr. | |
| 5,142,484 A | 8/1992 | Kaufman et al. | |
| 5,231,993 A | 8/1993 | Haber et al. | |
| 5,353,802 A | 10/1994 | Ollmar | |
| 5,471,382 A | 11/1995 | Tallman et al. | |
| 5,580,794 A | 12/1996 | Allen | |
| 5,633,910 A | 5/1997 | Cohen | |
| 5,642,731 A | 7/1997 | Kehr | |
| 5,724,580 A | 3/1998 | Levin et al. | |
| 5,737,539 A | 4/1998 | Edelson et al. | |
| 5,764,923 A | 6/1998 | Tallman et al. | |
| 5,789,675 A | 8/1998 | Blaine et al. | |
| 5,823,948 A | 10/1998 | Ross, Jr. et al. | |
| 5,833,625 A | 11/1998 | Essen-Moller | |
| 5,845,255 A | 12/1998 | Mayaud | |

(Continued)

FOREIGN PATENT DOCUMENTS

EP    0 274 363 B1    7/1988
(Continued)

OTHER PUBLICATIONS

"High-tech revolutionizes home health care", Health Day, Azcentral.com, Jan. 21, 2005, pp. 1-2.

(Continued)

*Primary Examiner* — Luke Gilligan

(57) ABSTRACT

A medical monitoring system that facilitates end-users in obtaining medical information concerning their health or wellness is disclosed. In one embodiment, an end-user is provided with a medical monitoring appliance. In another embodiment, an end-user acquires an appropriate medical monitoring appliance. The end-user can utilize the medical monitoring appliance to capture health data concerning the end-user. The health data can be electronically stored at a central repository and be available for electronic access by medical personnel and/or the end-user. The invention also facilitates remote evaluation of an end-user's health data by another person, such as a medical specialist.

23 Claims, 17 Drawing Sheets

U.S. PATENT DOCUMENTS

| | | |
|---|---|---|
| 5,875,108 A | 2/1999 | Hoffberg et al. |
| 5,880,826 A | 3/1999 | Jung et al. |
| 5,901,246 A | 5/1999 | Hoffberg et al. |
| 5,913,834 A | 6/1999 | Francais |
| 5,928,168 A | 7/1999 | Laros, Jr. |
| 5,938,593 A | 8/1999 | Ouellette |
| 5,946,659 A | 8/1999 | Lancelot et al. |
| 5,964,700 A | 10/1999 | Tallman et al. |
| 6,014,630 A | 1/2000 | Jeacock et al. |
| 6,017,315 A | 1/2000 | Starr et al. |
| 6,032,119 A | 2/2000 | Brown et al. |
| 6,039,688 A | 3/2000 | Douglas et al. |
| 6,081,750 A | 6/2000 | Hoffberg et al. |
| 6,118,521 A | 9/2000 | Jung et al. |
| 6,139,494 A | 10/2000 | Cairnes |
| 6,187,291 B1 | 2/2001 | Weinstein et al. |
| 6,222,620 B1 | 4/2001 | Jung et al. |
| 6,239,868 B1 | 5/2001 | Jung et al. |
| 6,246,471 B1 | 6/2001 | Jung et al. |
| 6,246,479 B1 | 6/2001 | Jung et al. |
| 6,248,067 B1 | 6/2001 | Causey, III et al. |
| 6,249,340 B1 | 6/2001 | Jung et al. |
| 6,249,348 B1 | 6/2001 | Jung et al. |
| 6,251,080 B1 | 6/2001 | Henkin et al. |
| 6,259,654 B1 | 7/2001 | de la Huerga |
| 6,271,913 B1 | 8/2001 | Jung et al. |
| 6,277,071 B1 | 8/2001 | Hennessy et al. |
| 6,294,999 B1 | 9/2001 | Yarin et al. |
| 6,302,844 B1 | 10/2001 | Walker et al. |
| 6,319,199 B1 | 11/2001 | Sheehan et al. |
| 6,362,888 B1 | 3/2002 | Jung et al. |
| 6,373,573 B1 | 4/2002 | Jung et al. |
| 6,375,469 B1 | 4/2002 | Brown |
| 6,400,996 B1 | 6/2002 | Hoffberg et al. |
| 6,414,750 B2 | 7/2002 | Jung et al. |
| 6,417,917 B1 | 7/2002 | Jung et al. |
| 6,418,424 B1 | 7/2002 | Hoffberg et al. |
| 6,436,058 B1 | 8/2002 | Krahner et al. |
| 6,443,890 B1 | 9/2002 | Schulze et al. |
| 6,449,041 B1 | 9/2002 | Jung et al. |
| 6,454,705 B1 | 9/2002 | Cosentino et al. |
| 6,519,037 B2 | 2/2003 | Jung et al. |
| 6,538,726 B2 | 3/2003 | DeJung et al. |
| 6,569,094 B2 | 5/2003 | Suzuki et al. |
| 6,573,984 B2 | 6/2003 | Jung et al. |
| 6,583,866 B2 | 6/2003 | Jung et al. |
| 6,590,660 B2 | 7/2003 | Jung et al. |
| 6,602,469 B1 | 8/2003 | Maus et al. |
| 6,610,012 B2 | 8/2003 | Mault |
| 6,612,984 B1 | 9/2003 | Kerr, II |
| 6,678,703 B2 | 1/2004 | Rothschild et al. |
| 6,847,892 B2 | 1/2005 | Zhou et al. |
| 6,942,616 B2 | 9/2005 | Kerr, II |
| 6,998,273 B1 | 2/2006 | Fleming et al. |
| 7,273,454 B2 | 9/2007 | Raymond et al. |
| 7,323,141 B2 | 1/2008 | Kirchhevel et al. |
| 7,366,675 B1 | 4/2008 | Walker et al. |
| 7,402,135 B2 | 7/2008 | Leveque et al. |
| 2001/0013006 A1 | 8/2001 | Brown |
| 2001/0034615 A1 | 10/2001 | Wilkinson et al. |
| 2001/0037215 A1 | 11/2001 | Sparks |
| 2001/0039504 A1 | 11/2001 | Linberg et al. |
| 2002/0001852 A1 | 1/2002 | Mendel-Hartvig et al. |
| 2002/0010597 A1 | 1/2002 | Mayer et al. |
| 2002/0016718 A1 | 2/2002 | Rothschild et al. |
| 2002/0019751 A1 | 2/2002 | Rothschild et al. |
| 2002/0022973 A1 | 2/2002 | Sun et al. |
| 2002/0026105 A1 | 2/2002 | Drazen |
| 2002/0035316 A1 | 3/2002 | Drazen |
| 2002/0038227 A1 | 3/2002 | Fey et al. |
| 2002/0049615 A1 | 4/2002 | Huber |
| 2002/0052761 A1 | 5/2002 | Fey et al. |
| 2002/0062225 A1 | 5/2002 | Siperco |
| 2002/0062230 A1 | 5/2002 | Morag et al. |
| 2002/0072933 A1 | 6/2002 | Vonk et al. |
| 2002/0072934 A1 | 6/2002 | Ross et al. |
| 2002/0077849 A1 | 6/2002 | Baruch et al. |
| 2002/0082480 A1 | 6/2002 | Riff et al. |
| 2002/0082865 A1 | 6/2002 | Bianco et al. |
| 2002/0087361 A1 | 7/2002 | Benigno et al. |
| 2002/0111559 A1 | 8/2002 | Kurata et al. |
| 2002/0120471 A1 | 8/2002 | Drazen |
| 2002/0188477 A1 | 12/2002 | Ackermann et al. |
| 2002/0198473 A1 | 12/2002 | Kumar et al. |
| 2003/0017440 A1 | 1/2003 | Bergey et al. |
| 2003/0023461 A1 | 1/2003 | Quintanilla et al. |
| 2003/0036683 A1 | 2/2003 | Kehr et al. |
| 2003/0067545 A1 | 4/2003 | Giron et al. |
| 2003/0086703 A1 | 5/2003 | Kollias et al. |
| 2003/0098580 A1 | 5/2003 | Christy |
| 2003/0108542 A1 | 6/2003 | Pruche et al. |
| 2003/0182162 A1 | 9/2003 | Stevens |
| 2003/0204132 A1 | 10/2003 | Suzuki et al. |
| 2003/0208108 A1 | 11/2003 | Shewmake et al. |
| 2003/0211007 A1 | 11/2003 | Maus et al. |
| 2004/0034284 A1 | 2/2004 | Aversano et al. |
| 2004/0034288 A1 | 2/2004 | Hennesy et al. |
| 2004/0037738 A1 | 2/2004 | Maus et al. |
| 2004/0038389 A1 | 2/2004 | Maus et al. |
| 2004/0039255 A1 | 2/2004 | Simonsen et al. |
| 2004/0044546 A1 | 3/2004 | Moore |
| 2004/0049355 A1 | 3/2004 | Maus et al. |
| 2004/0078211 A1 | 4/2004 | Schramm-Apple et al. |
| 2004/0078220 A1 | 4/2004 | Jackson |
| 2004/0078231 A1 | 4/2004 | Wilkes et al. |
| 2004/0086456 A1 | 5/2004 | Shirai |
| 2004/0122706 A1 | 6/2004 | Walker et al. |
| 2004/0122790 A1 | 6/2004 | Walker et al. |
| 2004/0125996 A1 | 7/2004 | Eddowes et al. |
| 2004/0133081 A1 | 7/2004 | Teller et al. |
| 2004/0139048 A1 | 7/2004 | Kerr, II et al. |
| 2004/0146290 A1 | 7/2004 | Kollias et al. |
| 2004/0171962 A1 | 9/2004 | Leveque et al. |
| 2004/0202685 A1 | 10/2004 | Manzo |
| 2004/0218810 A1 | 11/2004 | Momma |
| 2004/0249672 A1 | 12/2004 | Bocionek et al. |
| 2004/0257439 A1 | 12/2004 | Shirai et al. |
| 2005/0005678 A1 | 1/2005 | Duranton |
| 2005/0021370 A1 | 1/2005 | Riff et al. |
| 2005/0027562 A1 | 2/2005 | Brown |
| 2005/0119539 A1 | 6/2005 | Bazin |
| 2005/0119551 A1 | 6/2005 | Maschke |
| 2005/0143675 A1 | 6/2005 | Neel et al. |
| 2006/0121548 A1 | 6/2006 | Robbins et al. |
| 2006/0231109 A1 | 10/2006 | Howell et al. |
| 2006/0241355 A1 | 10/2006 | Howell et al. |
| 2006/0248946 A1 | 11/2006 | Howell et al. |
| 2007/0024465 A1 | 2/2007 | Howell et al. |
| 2007/0048224 A1 | 3/2007 | Howell et al. |
| 2007/0249059 A1 | 10/2007 | Stewart |
| 2008/0068559 A1 | 3/2008 | Howell et al. |
| 2008/0146890 A1 | 6/2008 | LeBoeuf et al. |
| 2008/0183287 A1 | 7/2008 | Ayre |
| 2008/0281168 A1* | 11/2008 | Gibson et al. ............ 600/301 |

FOREIGN PATENT DOCUMENTS

| | | |
|---|---|---|
| EP | 1 184 663 A2 | 3/2002 |
| EP | 1306783 A1 * | 5/2003 |
| GB | 2226879 | 7/1990 |
| JP | 02120652 A | 5/1990 |
| JP | 2003028794 A | 1/2003 |
| JP | 2004-236794 | 8/2004 |

OTHER PUBLICATIONS

Choi, Candice, "Virtual Medical Checkups on the Rise," ABC News, 2006, http://abcnews.go.com/Health/print?id=1715941, downloaded Mar. 15, 2006.

Marketing Devices, http://www.courage-khazaka.de/products/marketing_products.htm, downloaded May 14, 2007, pp. 1-4.

Courage+Khazaka electronic, "Measurement of Skin and Hair at the Point of Sale", Marketing brochure, complete catalogue for skin type analysis devices, http://www.courage-khazaka.de/download/pdf/brochure_marketing_lo.pdf, downloaded Feb. 11, 2008, 17 pages.

Products for Dermatology, http://www.courage-khazaka.de/products/derma_products.htm, downloaded May 14, 2007, pp. 1-4.

Scientific Devices, http://www.courage-khazaka.de/products/scientific_rd_prod.htm, downloaded May 14, 2007, pp. 1-5.
Étude, "The Way to skin counseling," Operation Manual, undated, front cover page and pp. 1-27.
"L'Oréal and STMicroelectronics applying semiconductors to skin aging," Press Release, Geneva, Oct. 18, 2002, pp. 2.
LifePoint Inc.—Saliva Based Testing Systems for the next generation, LifePoint® IMPACT® Test System, undated, 2 pages.
Our Solutions, Carematix Wellness System, Carematix Inc., 2002, 1 page.
Skin Care and Aging, U.S. National Institutes of Health, National Institute on Aging, last updated Dec. 29, 2005, pp. 1-7.
ViOptix :: Technology, How ODIS Works, copyright 2006, VIOptix, Inc., http://www.vioptix.com/docs/technology/howitworks.asp, downloaded Nov. 29, 2006, pp. 1-2.
ViOptix, Technology Overview, copyright 2006, VIOptix, Inc., http://www.vioptix.com/docs/technology/technology.asp., downloaded Dec. 5, 2006, pp. 1.
Wireless Assistant for Physicians and Relatives of Hospitalized Patients, UCLA Technology Available for Licensing, http://www.researchucla.edu/tech, Publ. No. US-2004-0073453-A1, 2001, 4 pages.
U.S. Appl. No. 10/397,641, filed Mar. 26, 2003.
U.S. Appl. No. 11/314,545, filed Dec. 20, 2005.
U.S. Appl. No. 11/888,723, filed Sep. 2, 2007.
U.S. Appl. No. 11/821,150, filed Jun. 22, 2007.
Moritex USA Incorporated, Sensors & Meters, copyright 2004, http://www.moritexusa.com/products/product_category.php?plid=5&pcid=10, downloaded Apr. 19, 2006, pp. 1-2.
"NOVA Technology Beams Up the Petite," ATSP Online, http://www.atsp.org/news/supplier.asp?contentID=863&FullStory=, downloaded May 14, 2007, pp. 1-6.
Physician Office Products, Chemstrip® Micral® Test Strips, Roche Diagnostics, 2004, 2 pages, downloaded Sep. 12, 2007.
Physician Office Products, Chemstrip® Urine Test Strips, Roche Diagnostics, 2004, 3 pages, downloaded Nov. 6, 2007.
Prince, R. "A disposable, self-administered Electrolyte Test," submitted to the Department of Electrical Engineering and Computer Science in partial fulfillment of the requirements for the degree of Master of Engineering in Electrical Engineering at the Massachusetts Institute of Technology, Feb. 2003, pp. 13-17.

\* cited by examiner

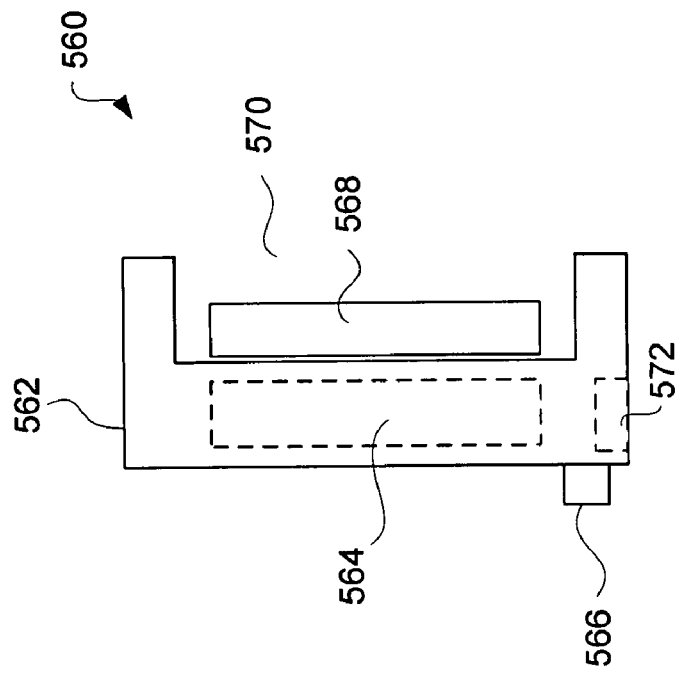
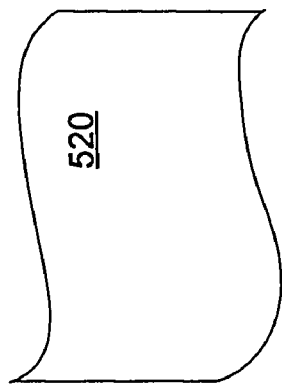
Fig. 5D
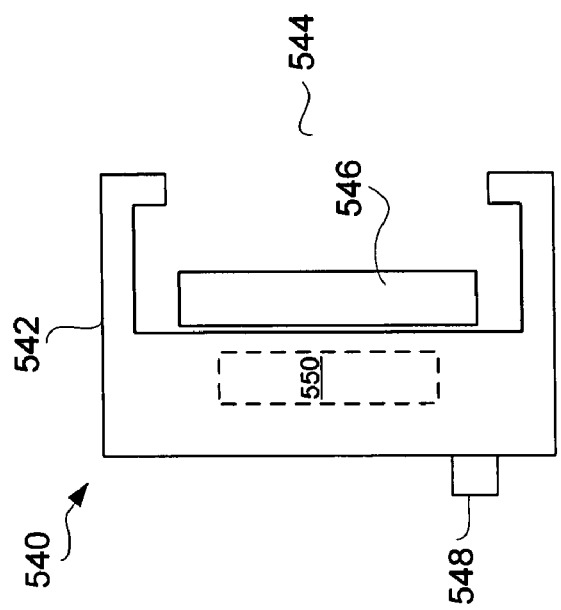

MEDICAL MONITORING SYSTEM

CROSS-REFERENCE TO RELATED APPLICATIONS

This application is related to a U.S. patent application Ser. No. 11/451,780, filed Jun. 12, 2006, entitled "HEALTHCARE BASE," and which is hereby incorporated herein by reference.

This application also claims priority benefit of: (i) U.S. Provisional Patent Application No. 60/785,825, filed Mar. 24, 2006, and entitled "MEDICAL MONITORING SYSTEM," which is hereby incorporated herein by reference; and (ii) U.S. Provisional Patent Application No. 60/880,308, filed Jan. 12, 2007, entitled "PORTABLE PRESSURE SENSOR AND HEART-BEAT SENSOR FOR PREGNANCY," and which is hereby incorporated herein by reference.

In addition, the following applications are made reference to: (i) U.S. patent application Ser. No. 11/314,545, filed Dec. 20, 2005, entitled "BOTTLE OF LOTION WITH A SENSOR," and which is hereby incorporated herein by reference; (ii) U.S. patent application Ser. No. 11/451,781, filed Jun. 12, 2006, entitled "PERSONAL AND PORTABLE BOTTLE," and which is hereby incorporated herein by reference; (iii) U.S. patent application Ser. No. 11/451,780, filed Jun. 12, 2006, entitled "HEALTHCARE BASE," and which is hereby incorporated herein by reference; (iv) U.S. patent application Ser. No. 11/479,665, filed Jun. 30, 2006, entitled "MOISTURE SENSOR FOR SKIN," and which is hereby incorporated herein by reference; (v) U.S. patent application Ser. No. 11/491,774, filed Jul. 22, 2006, entitled "PORTABLE CONTAINER WITH SPEAKER ATTACHED," and which is hereby incorporated herein by reference; (vi) U.S. patent application Ser. No. 11/592,431, filed Nov. 2, 2006, entitled "METHOD AND APPARATUS TO SENSE HYDRATION LEVEL OF A PERSON," and which is hereby incorporated herein by reference; (vii) U.S. Provisional Patent Application No. 60/636,969, filed Dec. 20, 2004, entitled "PREVENTIVE MEDICAL SYSTEMS, METHODS AND APPARATUS," and which is hereby incorporated herein by reference; (viii) U.S. Provisional Patent Application No. 60/652,213, filed Feb. 14, 2005, entitled "PREVENTIVE MEDICAL SYSTEMS, METHODS AND APPARATUS," and which is hereby incorporated herein by reference; (ix) U.S. Provisional Patent Application No. 60/670,957, filed Apr. 13, 2005, entitled "BOTTLE OF LOTION WITH A LOTION SENSOR," and which is hereby incorporated herein by reference; (x) U.S. Provisional Patent Application No. 60/689,312, filed Jun. 10, 2005, entitled "PERSONAL AND PORTABLE BOTTLE," and which is hereby incorporated herein by reference; and (xi) U.S. Provisional Patent Application No. 60/732,925, filed Nov. 2, 2005, entitled "METHOD AND APPARATUS TO SENSE HYDRATION LEVEL OF A PERSON," and which is hereby incorporated herein by reference.

FIELD OF THE INVENTION

The present invention relates to medical monitoring and, more particularly, to medical monitoring with end-user participation.

BACKGROUND OF THE INVENTION

Traditionally, a person schedules an appointment with a medical provider (e.g., a doctor), and then visits the medical provider on the scheduled time. During the appointment, the medical provider can perform a health or wellness check-up for the person. In some instances, the person might be due for a diabetes checkup, a hearing checkup, etc. In other instances, the person may be interested in particular medical conditions. For example, the person might have a skin discoloration that would like to have check to see if it is skin cancer. Unfortunately, for all these checkups and medical evaluations, the person must visit the medical provider's office which is time consuming and inconvenient for the person. Moreover, medical providers typically charge patients per office visit so the cost to the person or their insurance company is significant. Accordingly, there continues to be a need for improved approaches for persons to have their health and wellness monitored.

SUMMARY OF THE INVENTION

The invention pertains to a medical monitoring system. The medical monitoring system facilitates end-users in obtaining medical information concerning their health or wellness. In one embodiment, an end-user is provided with a medical monitoring appliance. In another embodiment, an end-user acquires an appropriate medical monitoring appliance. The end-user can utilize the medical monitoring appliance to capture health data concerning the end-user. The health data can be electronically stored at a central repository and be available for electronic access by medical personnel and/or the end-user. The invention also facilitates remote evaluation of an end-user's health data by another person, such as a medical specialist.

The invention can be implemented in numerous ways, including as a system, device, apparatus, and method. Several embodiments of the invention are discussed below.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIGS. 5D-5F illustrate how devices according to another embodiment of the invention can be utilized in acquiring appropriate images by an end-user.

DETAILED DESCRIPTION OF THE INVENTION

The invention pertains to a medical monitoring system. The medical monitoring system facilitates end-users in obtaining medical information concerning their health or wellness. In one embodiment, an end-user is provided with a medical monitoring appliance. In another embodiment, an end-user acquires an appropriate medical monitoring appliance. The end-user can utilize the medical monitoring appliance to capture health data concerning the end-user. The health data can be electronically stored at a central repository and be available for electronic access by medical personnel and/or the end-user. The invention also facilitates remote evaluation of an end-user's health data by another person, such as a medical specialist.

Embodiments of the invention are discussed below with reference to FIGS. 1-11. However, those skilled in the art will readily appreciate that the detailed description given herein with respect to these figures is for explanatory purposes as the invention extends beyond these limited embodiments.

Figure 1:
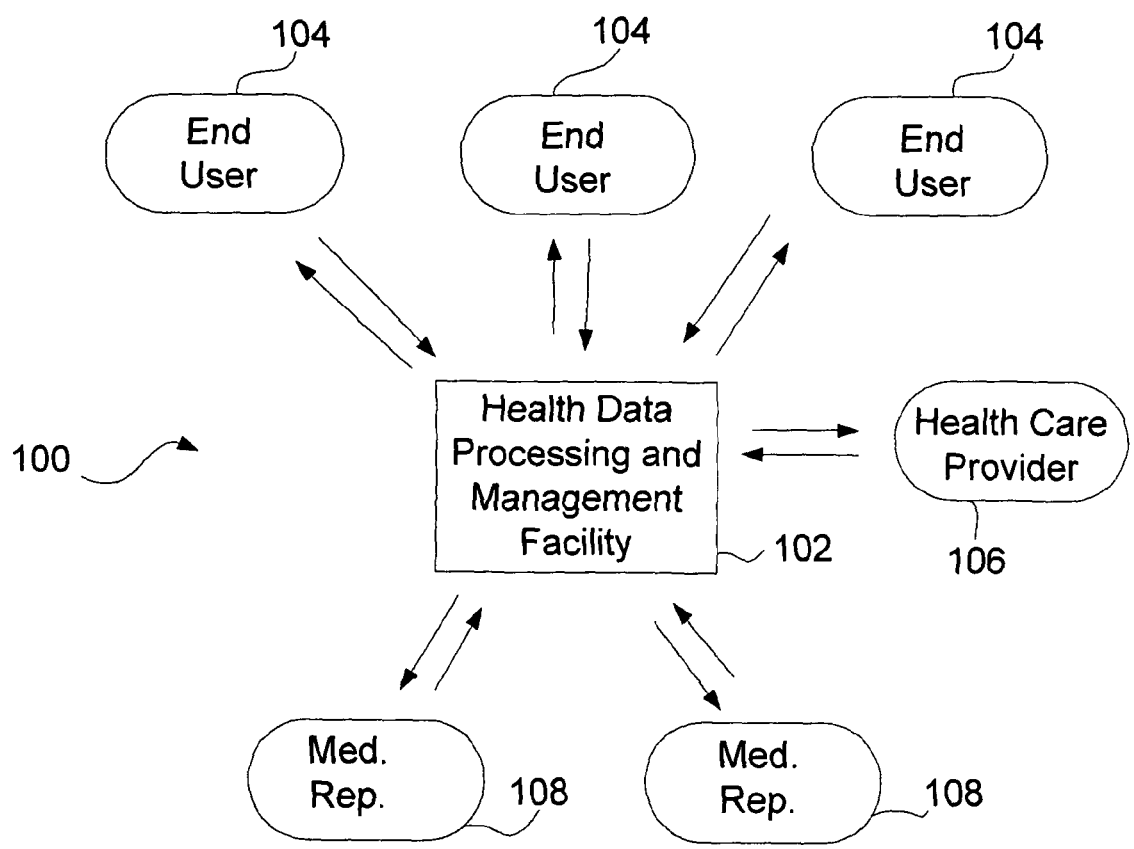
FIG. 1 is a distributed health and wellness system according to one embodiment of the invention.

FIG. 1 is a distributed health and wellness system 100 according to one embodiment of the invention. The health and wellness system 100 is distributed in that it utilizes resources, which can be both personnel and electrical equipment, located in one or more different locations.

In one embodiment, the distributed health and wellness system 100 includes a health and data processing and management facility 102. The health data processing and management facility 102 controls the overall operation of the distributed health and wellness system 100. In particular, the health data processing and management facility 102 is able to interact with a plurality of end-users 104. An end-user 104 is a person whose health or wellness is being monitored by the distributed health and wellness system 100. Through interaction with the end-users 104, the health data processing and management facility 102 operates to acquire health and wellness data (hereafter "health data") from the end-users 104. The acquired health data can be stored and managed by the health data processing and management facility 102. In addition, health-care providers 106 can be permitted to access the health data processing and management facility 102. Hence, the health data processing and management facility 102 facilitates the health care providers 106 in gaining access to the health data stored and maintained by the health data processing and management facility 102. Moreover, medical representatives 108 can interact with the health data processing and management facility 102. The medical representatives 108 can be trained medical professionals, nurses, medical technicians, etc. The medical representatives 108 can also gain access to the health data stored and maintained by the health data processing and management facility 102. The medical representatives 108 can be associated with, or independent of, the health-care providers 106.

According to one aspect of the invention, the distributed health and wellness system 100 is distributed. For example, the end-users 104 participate in the acquisition of their health data. The acquired health data is then transmitted from an end-user's location (e.g., home, office or local clinic) to the health data processing and management facility 102, which serves as a central processing facility. The health care providers 106 need not be located at the health data processing and management facility 102. Instead, the health care providers 106 can be provided with electronic access to the health data stored and/or maintained at the health data processing and management facility 102. Likewise, the medical representatives 108 can be geographically located away from the end-users, such as at other parts of the world. However, the medical representatives 108 can gain access to the health data stored and maintained by the health data processing and management facility 102.

In one embodiment, the medical representatives 108 are utilized to analyze the health data that is stored and maintained by the health data processing and management facility 102. In this regard, a particular medical representative 108 can specialize in evaluating health data for particular problematic health conditions. With electronic access to the health data and assistance from the health data processing and management facility 102, a particular medical representative 108 is able to efficiently handle and/or analyze health data regarding specific problematic health conditions for a number, which can be a large number of end-users 104. For example, the particular medical representative 108 may be highly trained at reviewing images of skin discolorations to evaluate presence of skin cancer conditions. In this regard, as an example, the health data processing and management facility 102 can facilitate end-users 104 in acquiring images of suspect skin regions on their bodies. The skin images that have been acquired from the end-user 104 can then be sent (electronically or manually) to the health data processing and management facility 102 and then stored by the health data processing and management facility 102. When or as appropriate, the medical representative 108 can examine the stored skin images to analyze whether a problematic skin condition exists, such as melanoma or skin cancer. Further, if there is a suspected problematic skin condition, the medical representative 108 can request (or the health data processing and management facility 102 can determine) that an appropriate health care provider 106 should be notified concerning the suspected problematic skin condition. The health data processing and management facility 102 can operate to so inform the health care provider 106. As appropriate, the health data processing and management facility 102 may also operate to inform the end-user 104 of the suspected problematic skin condition.

Given that the particular medical representative 108 can be specialized and can be located anywhere electronic network (e.g., Internet) access is available, the cost of the analysis can be reduced. As an example, the particular medical representative 108 can be a doctor, such as a doctor experienced in analyzing skin conditions. The doctor, referred to as a primary doctor, can be assisted by a team of junior doctors and other medical practitioners. The initial review of the health data can be by the lower cost medical practitioners. If desired, multiple independent reviews of the same health data can be performed for even greater certainty. Subsequent review by the junior doctors can then be performed on a subset of the health data that potentially have suspected problematic skin conditions, and then still a further subset of the health data can be reviewed by the primary doctor. The health data can also be reviewed by a computer. The computer evaluation can be initially performed as to assist or aid practitioners in reviewing the health data or can be performed as requested by a practitioner, health care provider or user. The computer evaluation can also be automatically performed, such as periodically or when new health data is available to be evaluated. Still further, the computer evaluation can serve to trigger manual evaluation or review of the health data be practitioners or health care providers.

The skin images acquired and processed, for example, as noted above, are typically optical images. Such optical images can, for example, be referred to as digital pictures. However, it should be noted that the skin images can differ in other embodiments. For example, in one embodiment, the skin images can pertain to thermal images. The thermal images can be acquired and processed to analyze whether a problematic skin condition exists. As an example, it is believed that cancerous cells tend to absorb or retain more heat, or take longer time to release heat absorbed, than healthy or non-cancerous cells. The thermal images can be processed to locate skin regions having such problematic conditions.

Figure 2:
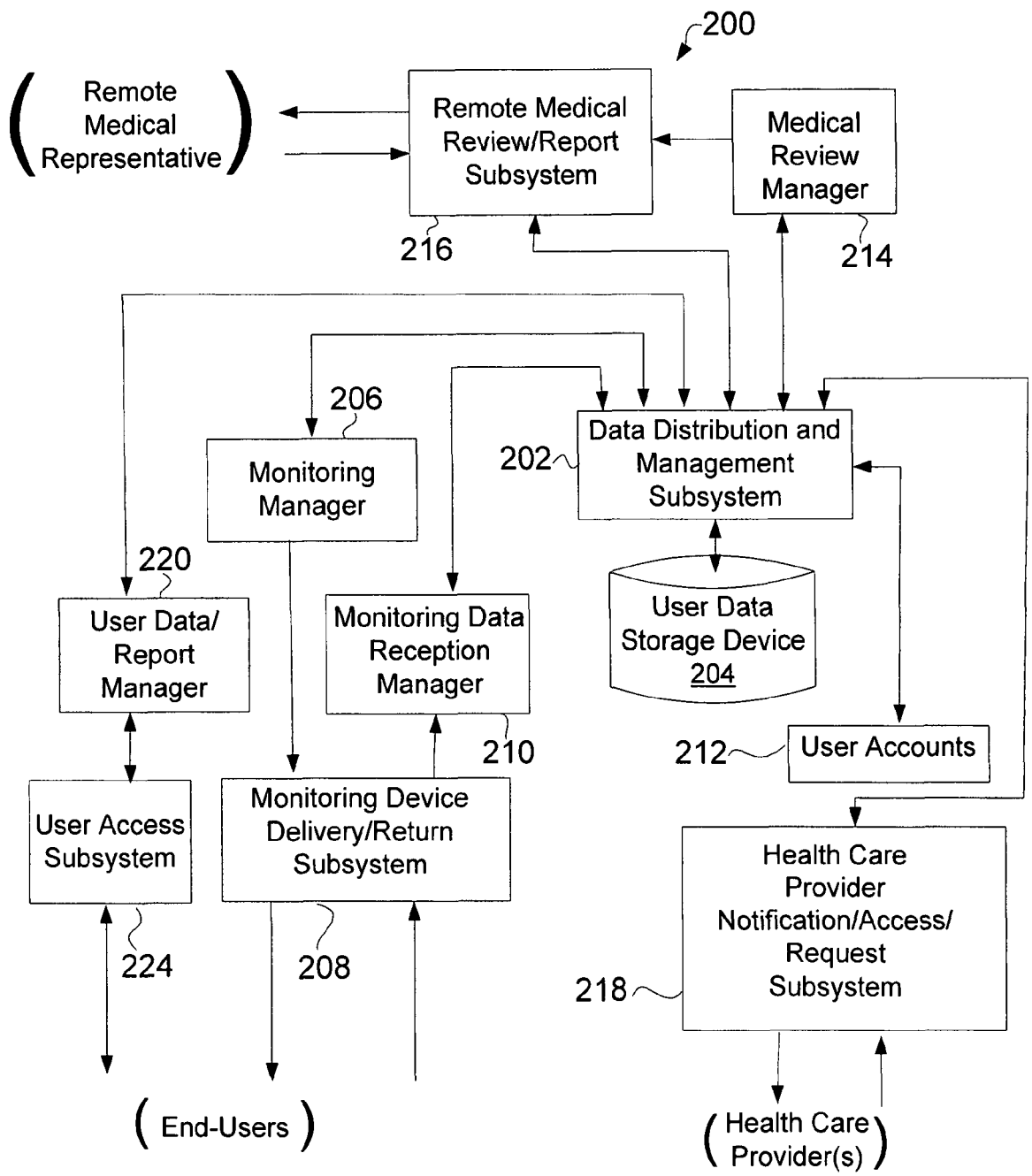
FIG. 2 is a block diagram of a health and wellness system according to one embodiment of the invention.

FIG. 2 is a block diagram of a health and wellness system 200 according to one embodiment of the invention. The health and wellness system 200 is, for example, suitable for use as the health data processing and management facility 102 illustrated in FIG. 1.

In one embodiment, the health and wellness system 200 includes various different subsystems. A data distribution and management subsystem 202 serves as a central subsystem for the health and wellness system 200. The data distribution and management subsystem 202 couples to a user data storage device 204. The user data storage device 204 can store health and wellness data for a plurality of end-users.

The health and wellness system 200 supports distributed health and wellness monitoring by the end-users. In this regard, the health and wellness system 200 includes a monitoring manager 206. The monitoring manager 206 oversees the monitoring of one or more health and wellness issues or conditions of the end-users. In one embodiment, the monitoring manager 206 couples to the data distribution and management subsystem 202 and a monitoring device delivery/return subsystem 208. The monitoring manager 206 determines when end-users are to monitor certain health and wellness conditions. When requested by the monitoring manager 206, the monitoring device delivery/return subsystem 208 provides (e.g., delivers) a monitoring device to an end-user. The monitoring device can be, for example, sent by a courier or by postal mail, to the end-user. The monitoring device provided to the end-user is utilized by the end-user to acquire health and wellness data pertaining to the user. The type of monitoring device can vary widely depending upon the type of health and wellness data to be acquired. For example, when the health and wellness stated to be acquired are images of skin regions, the monitoring device can be an image capture device. Upon receiving the monitoring device, the end-user then utilizes the monitoring device to acquire the desired health and wellness data (e.g., images of skin regions). The monitoring device then can be returned to the monitoring device delivery/return subsystem 208.

When the returned monitoring device is received by the monitoring device delivery/return subsystem 208, a monitoring data reception manager 210 extracts the health and wellness data from the returned monitoring device and provides such data to the data distribution and management subsystem 202, which causes the health and wellness data to be stored in the user data storage device 204. The data distribution and management subsystem 202 can also process the incoming health and wellness data prior to or after being initially stored in the user data storage device 204. The health and wellness data can also be referred to as user data. For example, the health and wellness data over a period of time may be processed (e.g., organized or correlated) through data processing operations so that the stored health and wellness data is more usable by health-care providers or medical representatives. Organizing the health and wellness data in a predetermined manner can provide a consistent data model that enables health care providers and medical representatives to efficiently review the stored health and wellness data.

The data distribution and management subsystem 202 can also maintain user accounts 212. The user accounts 212 provide personal information regarding the users (name, address, age, social security number, insurance information, etc.), authorizations for data access that they have approved, their health-care provider, medical group, etc. The user accounts 212 can also store user requests, conditions or preferences for types of health and wellness conditions to be monitored. With health and wellness data for a given user stored in the user data storage device 204, the data distribution and management subsystem 202 can determine that remote medical personnel should review the health and wellness data. In this regard, the data distribution and management subsystem 202 can interact with a medical review manager 214. The medical review manager 214 can coordinate the medical review of health and wellness data for one or more users with remote medical representative. The medical review manager 214 is operatively connected to the data distribution and management subsystem 202 and to a remote medical review/report subsystem 216. When the medical review manager 214 desires to have a remote medical representative review the health and wellness data for one or more users, the medical review manager 214 interacts with the remote medical review/report subsystem 216. The remote medical review/report subsystem 216 can then operate to forward appropriate requests and health and wellness data (or access thereto) to a remote medical representative. The remote medical representative then is able to review the health and wellness data and can prepare a report regarding his/her review. The report is typically provided as an electronic report. The report is then returned to the remote medical review/report subsystem 216 which can cause the report to be stored by the data distribution and management subsystem 202 in the user data storage device 204.

Depending upon the nature of the report, a health-care provider (e.g., the user's primary care physician) may be consulted regarding the health and wellness data of the user. The health-care provider could be notified when the data distribution and management subsystem 202 detects certain conditions. Such notifications can be computerized or automatic. For example, the data distribution and management subsystem 202 can process the health and wellness data to determine whether suspect health conditions exist. Nevertheless, when the data distribution and management subsystem 202 desires to interact with a health-care provider, a health-care provider notification/access/request subsystem 218 is utilized. The health-care provider notification/access/request subsystem 218 allows a health-care provider to (i) be notified, (ii) access health and wellness data from the user data storage device 204, and (iii) request certain monitoring to be performed (either by the health-care provider or by the end-user).

The health and wellness system 200 can also produce a user data report suitable for distribution to an end-user. Typically, the health and wellness system 200 would produce a user report to provide health and wellness data to an end-user in a useful and user-friendly manner. A user data/report manager 220 can be used to generate a user data report for an end-user.

For example, a user preference as specified by the user may have specified periodic user reports to be provided to the end-user. On the other hand, the data distribution and management subsystem 202 alone or together with the user data/report manager 220 can determine when it is an appropriate time to provide user reports to end-users. In any case, when the user data/report manager 220 determines that a user report is to be provided to an end-user, a user access subsystem 224 permits a user report to be provided to the end-user, or permits the end-user to access the user report available from the user data/report manager 220.

As noted above, the health and wellness data acquired by the monitoring device can pertain to images of skin regions. In one embodiment, the images can pertain to radiation in a visible range, which can be known as pictures or photographs. In another embodiment, the images can pertain to other sources, such as radiation in an infrared range, which can be known as thermal images. However, the health and wellness data used with the health and wellness system 200 can be various other types of data as acquired by a monitoring device. For example, the health and wellness data that can be acquired, such as heart, kidney or lung performance data, chemical reaction data, etc. In one embodiment, the chemical reaction data results from a chemical to a bodily secretion. The health and wellness data can be used to monitor various illnesses, including asthma, diabetes, heart disease, HIV, lung disease, kidney disease, etc.

Figure 3A:
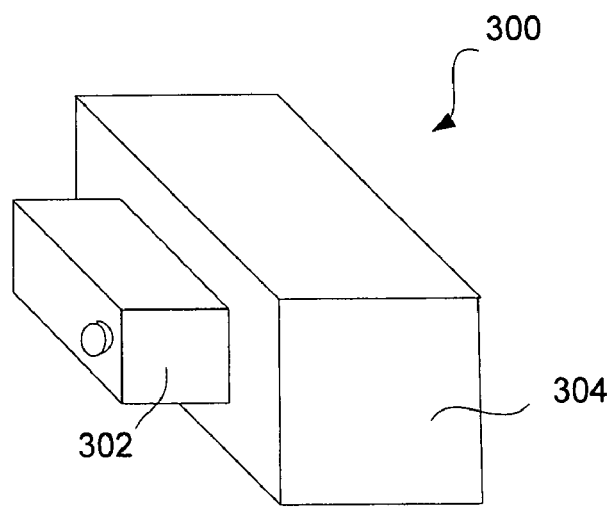
FIG. 3A is a perspective view of a skin monitoring system according to one embodiment of the invention.

FIG. 3A is a perspective view of a skin monitoring system 300 according to one embodiment of the invention. The skin monitoring system 300 includes a camera 302 and a guide box 304. The skin monitoring system 300 is designed to facilitate capturing of skin images by end-users.

Figure 3B:
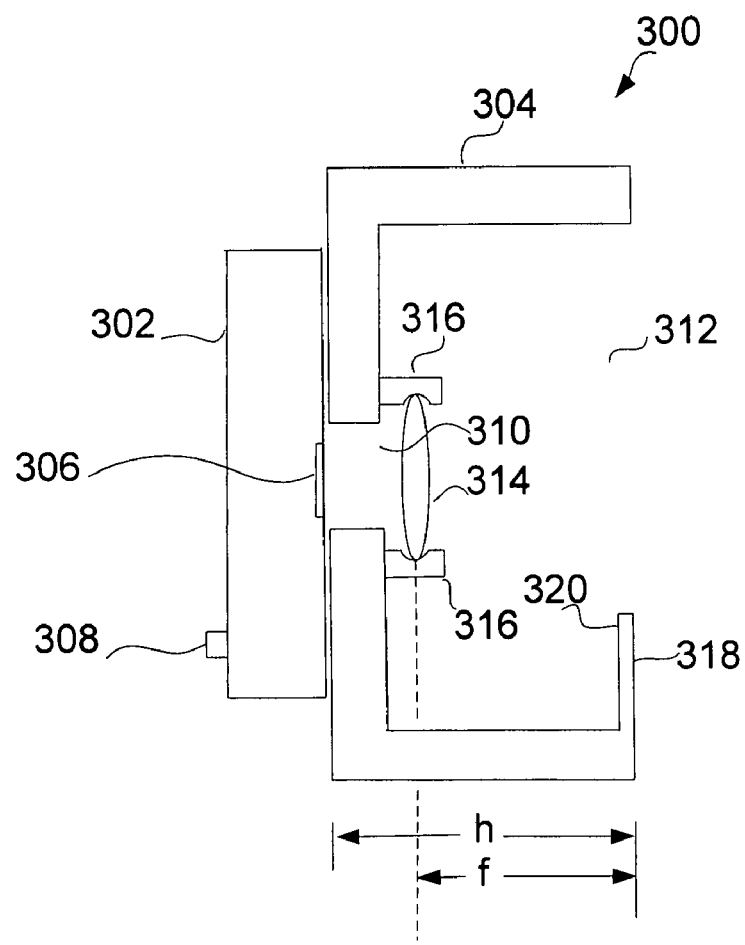
FIG. 3B is a cross-sectional view of the skin monitoring system illustrated in FIG. 3A according to one embodiment of the invention.

FIG. 3B is a cross-sectional view of the skin monitoring system 300 illustrated in FIG. 3A according to one embodiment of the invention. As shown in FIG. 3B, the guide box 304 has a smaller opening 310 proximate to the camera 302, and a larger opening 312 at the opposite end of the guide box 304. The camera 302 is attached to the guide box 304. In one embodiment, the camera 302 is removably attached to the guide box 304. Internal to the guide box 304 is a lens 314. When the camera 302 is attached to the guide box 304, an aperture 306 for the camera is aligned with the lens 314. The lens 314 can be held in position by lens holders 316. Although the opening 312 of the guide box 304 is a substantial portion of the area at that end of the guide box 304, the guide box 304 can include a partial back surface 318. On the interior side 320 of the partial back surface 318 there can be provided a ruler or other markings. Such a ruler or markings can assist with the understanding of the size, nature or characteristics of an image or part of an image being captured. For example, when an image is acquired using the skin monitoring system 300, the image will include the ruler or other markings, which provide a reference. The guide box 304 has a height (h), and has a distance (f) from the end of the guide box 304 to the lens 314, which is the focusing distance of the lens 314. Hence, when the skin monitoring system 300 is utilized to capture skin images, the images are typically properly in focus, or otherwise acquired in a controlled environment. A push button 308 on the camera 302 allows the user to capture an image using the camera 302. The aperture 306 can also include a lens.

Although not show in FIGS. 3A and 3B, the skin monitoring system 300 can also include a light or flash device so as to provide light during capture of the skin images. For example, the light or flash device can provide light that is white, red, blue, infrared ultraviolet, or other color that is useful for imaging the skin region being analyzed. In one embodiment, the light or flash is provided by the camera 302. For example, the light or flash device could be adjacent to the opening 312 of the guide box 304 or at another opening that can be provided in the guide box 304. In another embodiment, the light or flash device could be attachable to the guide box 304. In still another embodiment, the light or flash can be provided by the guide box 304. In this situation, the light or flash device would be internal to the guide box 304 and controlled by a switch. In any case, the light or flash device serves to provide uniform or appropriate lighting for image capture so that images can be relatively consistently properly exposed.

Figure 4A:
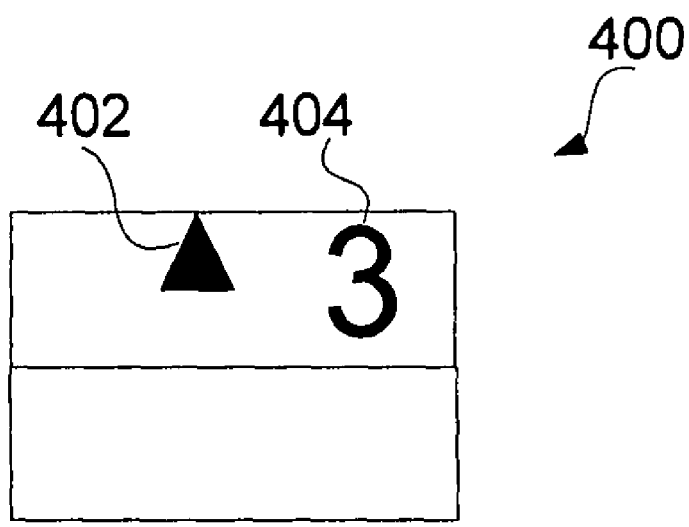
FIG. 4A is a view of a skin reference device according to one embodiment of the invention.

FIG. 4A is a view of a skin reference device 400 according to one embodiment of the invention. A user can utilize the skin reference device 400 to provide a reference at any skin area that is being captured by a camera or a skin monitoring system. The skin reference device 400 includes a pointer 402 and a reference number 404. The skin reference device 400 can, for example, be a label that can be placed on an end-user's skin such that the pointer 402 points to the skin condition, mark or area that is to be captured by the system. Hence, when the image (e.g., picture or photo) of the skin condition, mark or area is captured, the image will include a depiction of the skin reference device 400. The reference number 404 can serve to provide a designator, which can be unique, for the skin condition, mark or area.

Figure 4B:
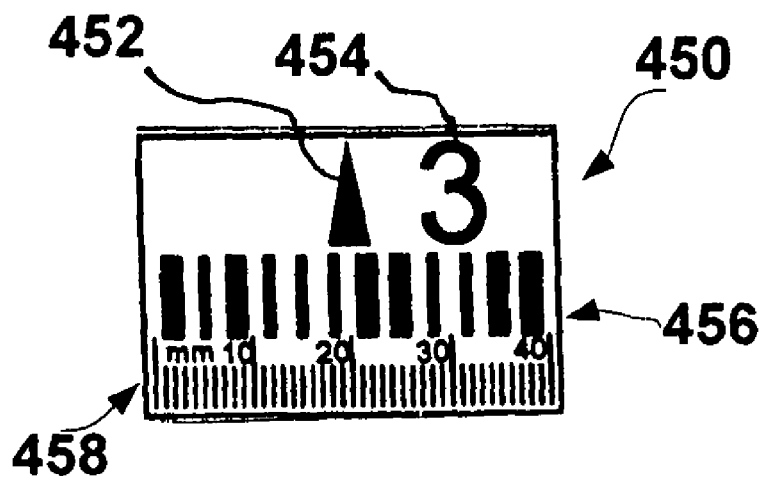
FIG. 4B is a view of a skin reference device according to another embodiment of the invention.

FIG. 4B is a view of a skin reference device 450 according to another embodiment of the invention. The skin reference device 450 includes a pointer 452, a reference number 454, a bar code 456, and a ruler 458. A user can utilize the skin reference device 450 to provide a reference at any skin area that is being captured by a camera or a skin monitoring system. The skin reference device 450 can, for example, be a label that can be placed on the end-user's skin such that the pointer 452 points to the skin condition, mark or area that is to be captured by a skin monitoring system. The bar code 456 can facilitate computerized recognition of the characteristics of the skin reference device 450. For example, the bar code 456 can signal to a computing system the reference number 454. The bar code 456 could also encode or be linked to various other information, such as user information, date, time, etc. The ruler 458 facilitates review of the captured images, namely, understanding the size of a particular mark on the skin, which can be subsequently evaluated from an acquired image. For example, the ruler 458 can allow a mark (e.g., lesion) to be compared over time, such as where the mark in a recently acquired image is of a different size (e.g., larger) than in a previously acquired image.

Figure 5A:
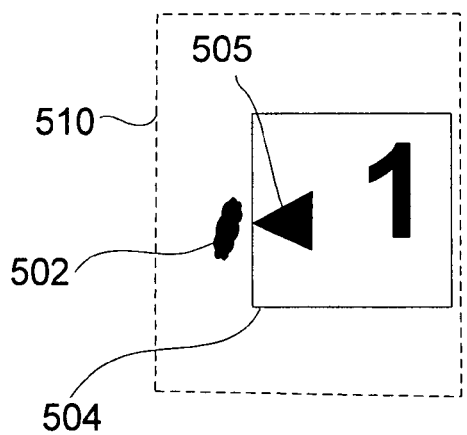
FIGS. 5A-5C illustrate how the skin reference devices can be utilized in acquiring appropriate images of skin conditions by an end-user according to one embodiment of the invention.
Figure 5B:
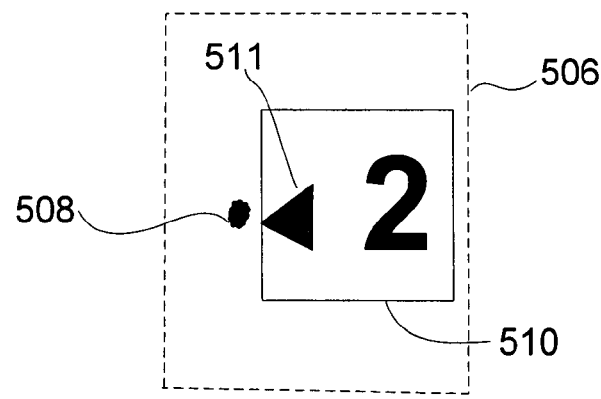
Figure 5C:
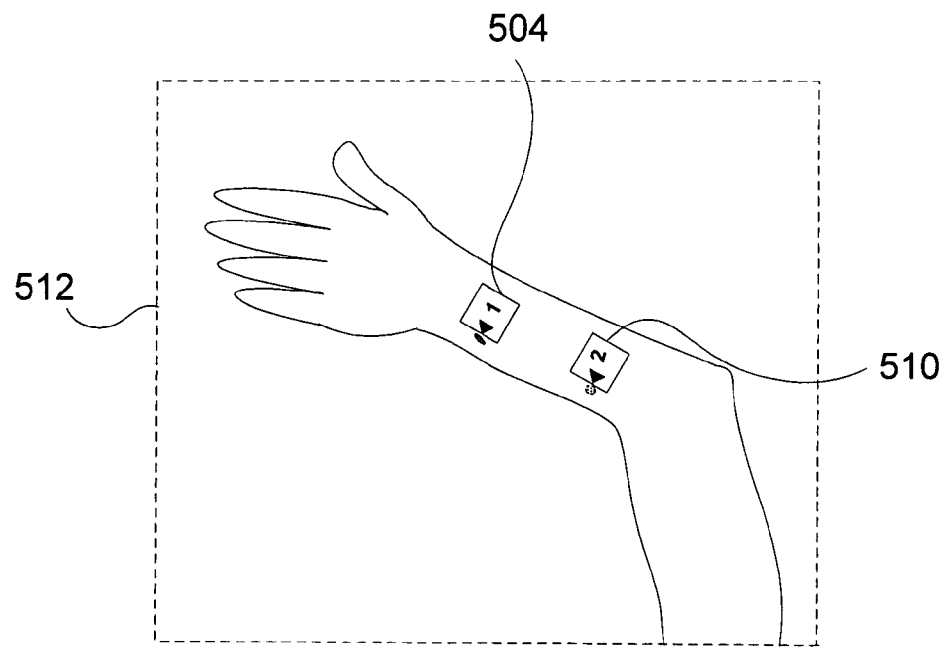

FIGS. 5A-5C illustrate how the skin reference devices according to one embodiment of the invention can be utilized in acquiring appropriate images of skin conditions by an end-user. The images of skin conditions are acquired by a skin monitoring system, such as the skin monitoring system 300 illustrated in FIGS. 3A and 3B.

In FIG. 5A, a skin reference device 504 is provided proximate to a skin condition 502. The pointer 505 of the skin reference device 504 is directed to the skin condition 502. Then, using the skin monitoring system, an image 500 of the skin condition 502 and the skin reference device 504 is captured. Similarly, in FIG. 5B, a skin reference device 510 is provided proximate to a skin condition 508. The pointer 511 of the skin reference device 510 is directed to the skin condition 508. Then, using the skin monitoring system, a second image 506 is captured. Note that the skin reference device 504 includes a reference number 1, and the skin reference device 510 includes a reference number 2. The images 500 and 506 can be considered close-up images of the skin conditions 502 and 508, respectively. Given the use of the skin monitoring system, the images 500 and 506 can be clear, properly exposed and in focus. However, capturing additional images from a perspective further from the skin surface can aid in the understanding of the precise position of the skin conditions being monitored with respect to other parts of the end-user's body. For example, in FIG. 5C, an image 512 includes a substantial portion of the end-user's arm. As shown in FIG. 5C, the skin reference devices 504 and 510 remain on the end-user's arm when the image 512 was acquired. Hence, the image 512 provides context as to where the skin conditions 502 and 508 reside with respect to the arm of the end-user.

A camera can be used to capture the images. In one implementation, the camera can have two different lens systems. In another implementation, the camera can have one lens with two different focal settings, with one focal setting used for the close-up images (e.g., images 500 and 506) and the other focal setting used for the context images (e.g., images 512).

In one embodiment, there can be a CCD array or other image detector(s) at the smaller opening 310, such as at the aperture 306. The lens 314 can be positioned at a focusing distance (f) so that for close-up pictures, the images (e.g., images 500 and 506) can be in focus at the image detector(s), such as at the aperture 306. For context pictures, the lens 314 can be moved closer to the aperture 306 to a different focusing distance (f) so that the context images (e.g., images 512) can be in better focus at the image detector(s). In one embodiment, there can be a small lever or other type of moving mechanisms to move the lens 314 from the close-up position to the context position. In another embodiment, the camera 302 can be a commercial camera, such as a disposable digital camera, with its own lens system. The lens 314, which can be a lens system, can be designed so that when the lens 314 is positioned at a focusing distance (f), close-up images (e.g. images 500 and 506) are in focus at the image plane of the camera. For context images (e.g. images 512), the lens 314 can be removed (or moved) to allow the camera to take pictures. In one embodiment, the lens 314 can be removed manually, and in another embodiment, the lens 314 can be moved by a mechanical system, such as a lever.

In one embodiment, when images are taken, they are also time-stamped to record when the images are taken. Since each image can be electronically identified relative to its position at the body of the end-user, multiple images of the same location can be compared relative to each other as a function of time. For example, images with reference number 1 are compared as a function of time. The images document the change or the lack of change of the skin condition 502 as a function of time. In one embodiment, when a medical representative is reviewing the images, the system automatically collects and organizes the images with the same reference number. Then they can be shown to the representative chronologically as a function of time on a screen. All the images can be shown on the screen simultaneously with a time-stamp indicated below each image. In another embodiment, only recent images are shown to show how a skin condition has been changing recently. For example, only images in the last twelve months can be, at least initially, shown to the medical representative.

In another embodiment, the system automatically performs image processing on the images pertaining to skin condition. For example, based on edge-recognition techniques, the system automatically identifies the size of a skin condition and computes the approximate area occupied by the skin condition. If the area changes by more than a preset percentage over a preset period of time, then the skin condition could be considered as a suspect skin condition. In such cases, a medical representative could be alerted to review the images.

According to another embodiment of the invention, thermal radiation can be measured and utilized to determine skin condition or other health conditions associated with a user. According to one implementation, skin associated with the user can be locally heated and then one or more thermal images are acquired at the corresponding skin region. The thermal image(s) acquired can be evaluated as discussed herein. More generally, an embodiment of the invention can first excite or induce a portion of the body by an excitation source, and then measure responsiveness to such excitation. As one example, the excitation can be a heat source to apply heat to a body portion (e.g., skin region), and the measurement can be thermal imaging of the body portion that has been previously heated. Thermal imaging can be done by a thermal image acquisition device, and the images can be used to determine, for example, the rate of heat dissipation by the previously heated body portion.

FIGS. 5D-5F illustrate how devices according to another embodiment of the invention can be utilized in acquiring appropriate images by an end-user. In the embodiment illustrated in FIGS. 5D-5F, images of skin conditions can be acquired. In one implementation the images being acquired are thermal images.

FIG. 5D illustrates a thermal wrap 520 according to one embodiment of the invention. The thermal wrap 520 can pertain to a piece of cloth, fabric, or other material that can be utilized to apply heat to a portion of a user's body. The thermal wrap 520 can also be considered a thermal blanket. The thermal wrap 520 can itself generate heat or can retain heat that was otherwise previously applied to the thermal wrap 520. In any case, the thermal wrap 520 can be placed on a portion of the body and utilized to heat that portion of the body. Typically, the portion of the body is associated with a region of skin on the body.

FIG. 5E illustrates a cross-sectional view of a heater 540 according to one embodiment of the invention. The heater 540 represents another approach to heating a portion of the body. The heater 540 includes a housing 542. One end of the housing 542 includes an opening 544. The end of the housing 542 having the opening 544 is applied against a portion on the user's skin. A heating element 546 provided within the housing 542 generates heat. The heat from the heating element 546 can be absorbed by the user's skin adjacent to the opening 544. In addition, the housing 542 also can include an on/off switch 548 that can be used to activate/deactivate the heating element 546. Still further, the housing 542 can include electrical circuitry 550 that is utilized to control the heating element 546 to produce the appropriate amount of heat. The on/off switch 548 can also be connected to the circuitry 550. The heater 540 can be powered by a battery provided within the housing 542 or it can be powered by an external source, e.g., external battery or an AC outlet via an electrical cord.

In FIG. 5E, the heating element 546 receded (or set back) from the opening 544. In another embodiment, the heating element 546 can be provided at the opening 544, and can be flexible or malleable to conform to the curvature of the skin or body part that is being heated. In such an embodiment, the heating element 546 can be in contact with the region to be heated.

FIG. 5F illustrates a cross-sectional view of an image acquisition device 560 according to one embodiment of the invention. The image acquisition device 560 includes a housing 562. The housing 562 includes internal circuitry 564, a switch 566, and a thermal imaging sensor 568. The thermal imaging sensor 568 is provided facing the end of the housing 562 having an opening 570. When the image acquisition device 560 is placed on a portion of the user's skin, the skin is adjacent to not only the opening 570 but also the thermal imaging sensor 568. The thermal image sensor 568 can then acquire one or more thermal images associated with the portion of the user's skin.

In one embodiment, the thermal imaging sensor 568 is represented by a two-dimensional arrangement of thermocouples arranged in a two-dimensional array. In another embodiment, the thermal imaging sensor 568 is a sheet of material with thermochromic paint. Thus, in this embodiment, instead of an infrared array or other image detector(s) at an aperture, such as the aperture 306 in FIG. 3B, the thermal imaging sensor can be a sheet of material whose characteristics change as a function of temperature.

In the embodiment shown in FIG. 5F, the imaging sensor 568 receded (or set back) from the opening 570. In another embodiment, the imaging sensor 568 can be provided at the opening 570, and can be malleable or flexible. For example, the thermal imaging sensor 568 includes a sheet of transparent plastic with thermochromic paint on a first surface. That first surface is at the opening 570, facing away from the inside of the housing 562. The plastic can conform to the surface to be measured to allow the thermochromic paint to be substantially in contact with the surface. There can be the thermal imaging sensor 568 (e.g., a digital camera) on the other side of the plastic, opposite to the first surface. With the plastic being transparent, the thermal imaging sensor 568 can take pictures of the thermochromic paint to register its color change.

The circuitry 564 can control the acquisition of a thermal image by the thermal imaging sensor 568, such as under the control of the switch 566. The circuitry 564 can also include circuitry (e.g., memory) to store the acquired thermal image. The image acquisition device 560 can optionally include a peripheral port 572, such as a USB port. The peripheral port 572 can be utilized to up-load data from the image acquisition device 560 to another electronic device, such as a personal computer.

In yet another embodiment, the image acquisition device and the heating device are integrated or incorporated in a package. One example is based on the transparent plastic sheet with thermochromic paint, as described above. There can be heating wires embedded in the plastic, such as in the configuration of a mesh. When current passes through the wires, the plastic heats up, and can be used as the heating device. When used as the image acquisition device, current is removed from the wires. Initially, the thermochromic paint still registers areas of elevated temperature due to the heating wires. After the heating wires have cooled off, the thermochromic paint can be used to image the temperature of the portion of the skin that the paint is adjacent.

Figure 6A:
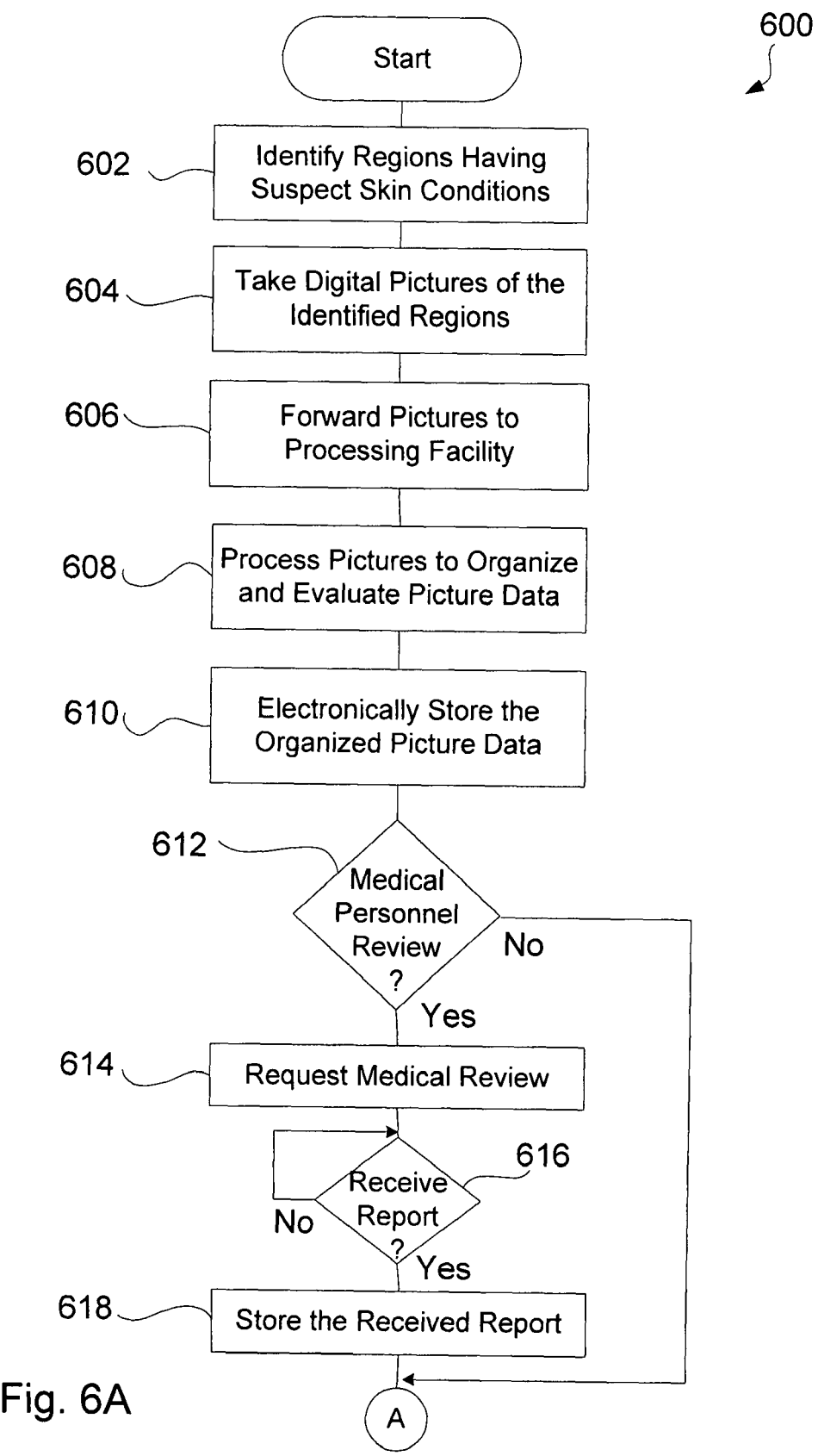
FIGS. 6A and 6B are flow diagrams of a skin monitoring process according to one embodiment of the invention.
Figure 6B:
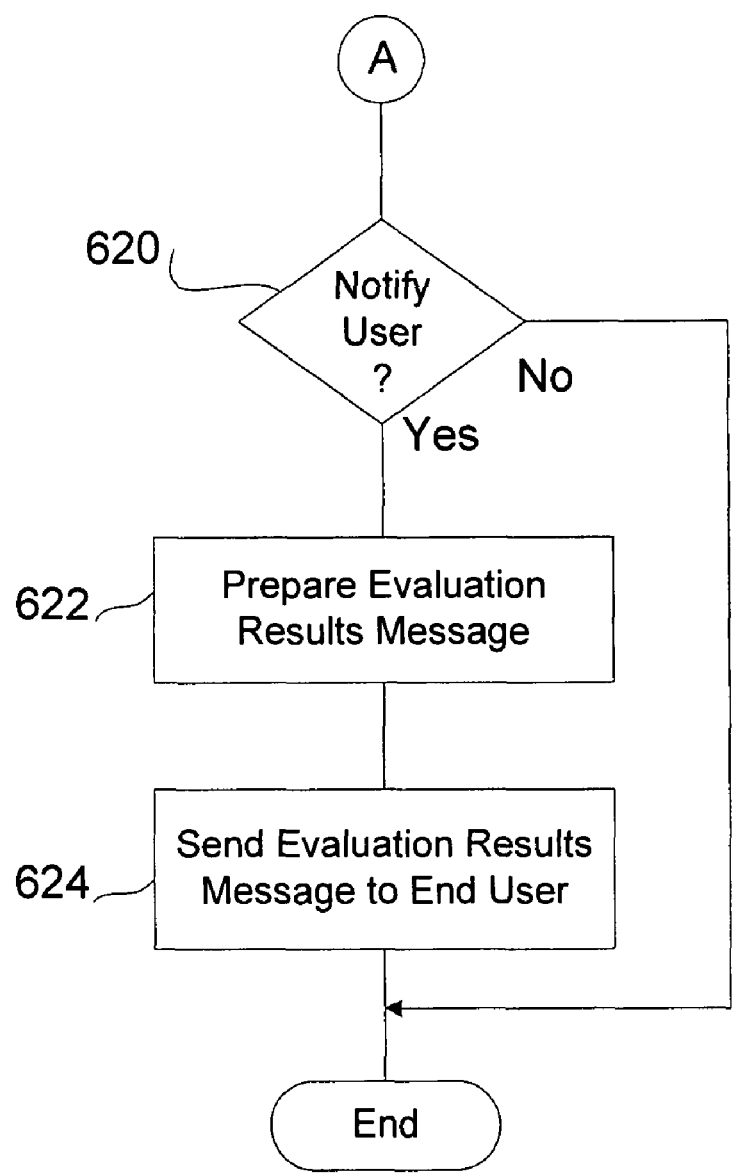

FIGS. 6A and 6B are flow diagrams of a skin monitoring process 600 according to one embodiment of the invention. The skin monitoring process 600 is, for example, performed by a user and a computing device.

The skin monitoring process 600 initially identifies 602 regions having suspect skin conditions. Then, digital pictures are taken 604 of the identified regions. In one embodiment, the digital pictures are taken 604 using a skin monitoring system, such as the skin monitoring system 300 illustrated in FIGS. 3A and 3B. After the digital pictures are taken 604, the digital pictures are forwarded 606 to a processing facility. The digital pictures can be forwarded 606 in a variety of different ways, including by courier, postal mail, electronic file transfer or electronic mail. The forwarding 606 of the pictures can involve the forwarding of the electronic data or can involve the forwarding of the skin monitoring system, or a camera portion thereof, that includes the digital pictures.

When the digital pictures arrive at the processing facility, the digital pictures are processed 608, which can include organizing and evaluating the picture data. The organized picture data is then electronically stored 610. Subsequently, a decision 612 determines whether medical personnel should review the picture data. When the decision 612 determines that medical personnel should review the picture data, a medical review is requested 614.

There can be different approaches to determine that medical personnel should review the picture data. In one embodiment, when picture data arrives, medical personnel will be alerted to review the arrived data. In another embodiment, the picture data can be initially electronically evaluated. For example, computerized processing at the processing facility can perform an evaluation of the picture data in an automated fashion. To illustrate, in the context of monitoring skin conditions, the electronic evaluation can monitor size, rate of growth, and/or color (pigmentation). Regarding monitoring the rate of growth, the electronic evaluation could check the picture data against prior picture data. If the electronic evaluation indicates one or more suspected regions, medical personnel can be summoned. Different embodiments have been described in electronically determining problematic images of skin problems in U.S. Patent Publications, 2005/0119551 A2 and 2004/0218810 A1, both of which are hereby incorporated herein by reference In response to the medical review request, a medical person can review and prepare a report regarding the picture data. Hence, the skin monitoring process 600 can await the reception of such a report. Here, a decision 616 determines whether a report has been received from a medical person. When the decision 616 determines that a report has not yet been received, the skin monitoring process 600 can await such a report, though other processing or acts can be performed while awaiting a report. Once the decision 616 determines that a report has been received, the received report is stored 618. Alternatively, when the decision 612 determines that medical review is not requested at this time, then blocks 614 through 618 are bypassed.

Following the block 618, or its being bypassed, a decision 620 determines whether the end-user should be notified. In one embodiment, the end-user can be notified after the medical review of the images. In another embodiment, the end-user can be notified if there are problematic images. In still another embodiment, user preferences provided by an end-user can determine or influence when the end-user is to be notified (and/or how). In yet another embodiment, notification of an end-user can be determined or influenced by a practitioner performing a review or by a health care provider.

The end-user can be notified of the medical data, the medical review/report, etc. when the decision 620 determines that the end-user is to be notified. When the end user is to be notified, an evaluation results message is prepared 622. The evaluation results message can include medical data, medical review/reports regarding the medical data, recommendations, preventative care treatments, and/or additional related information. After the message is prepared, the evaluation results message is sent 624 to the end-user. The evaluation results message can be sent 624 in a variety of different ways, including such as by courier, postal mail, electronic file transfer or electronic mail. Alternatively, when the decision 620 determines that the end-user is not to be notified, the blocks 622 and 624 are bypassed. Following the blocks 624, or its being bypassed, the skin monitoring process 600 is complete and ends. In one embodiment, the blocks 602 and 604 are performed by or with the assistance of end-users, whereas the blocks 606-624 are performed by one or more computing devices.

Figure 6C:
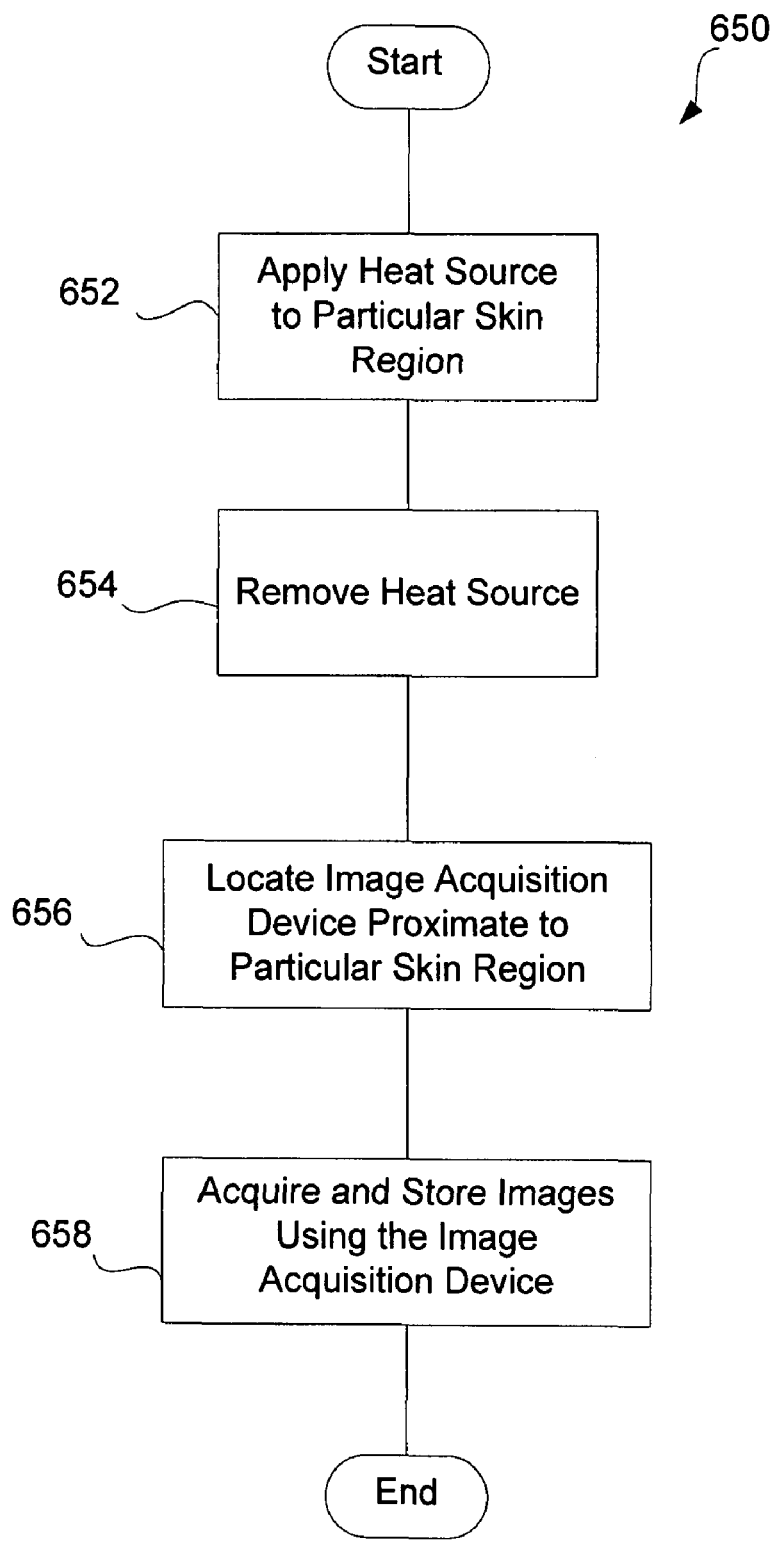
FIG. 6C is a flow diagram of an image acquisition process according to one embodiment of the invention.

FIG. 6C is a flow diagram of an image acquisition process 650 according to one embodiment of the invention. The image acquisition process 650 can, for example, be performed by a user utilizing a thermal wrap or heater as well as an image acquisition device.

The image acquisition process 650 initially can apply 652 a heat source to a particular skin region. Here, the heat source produces heat that is transferred to the particular skin region. After the appropriate amount of heating of the particular skin region, the heat source can be removed 654. Then, an image acquisition device can be located 656 proximate to the particular skin region. Thereafter, one or more images of the particular skin region can be acquired and stored 658 using, for example, the image acquisition device. In this embodiment, the images are thermal images associated with a thermal mapping of the particular skin region in response to the prior heating of such region. Following the block 658, the image acquisition process 650 can end. Once the thermal images are acquired, the thermal images can be processed and evaluated, such as by processes similar to processing other images discussed herein.

Figure 7:
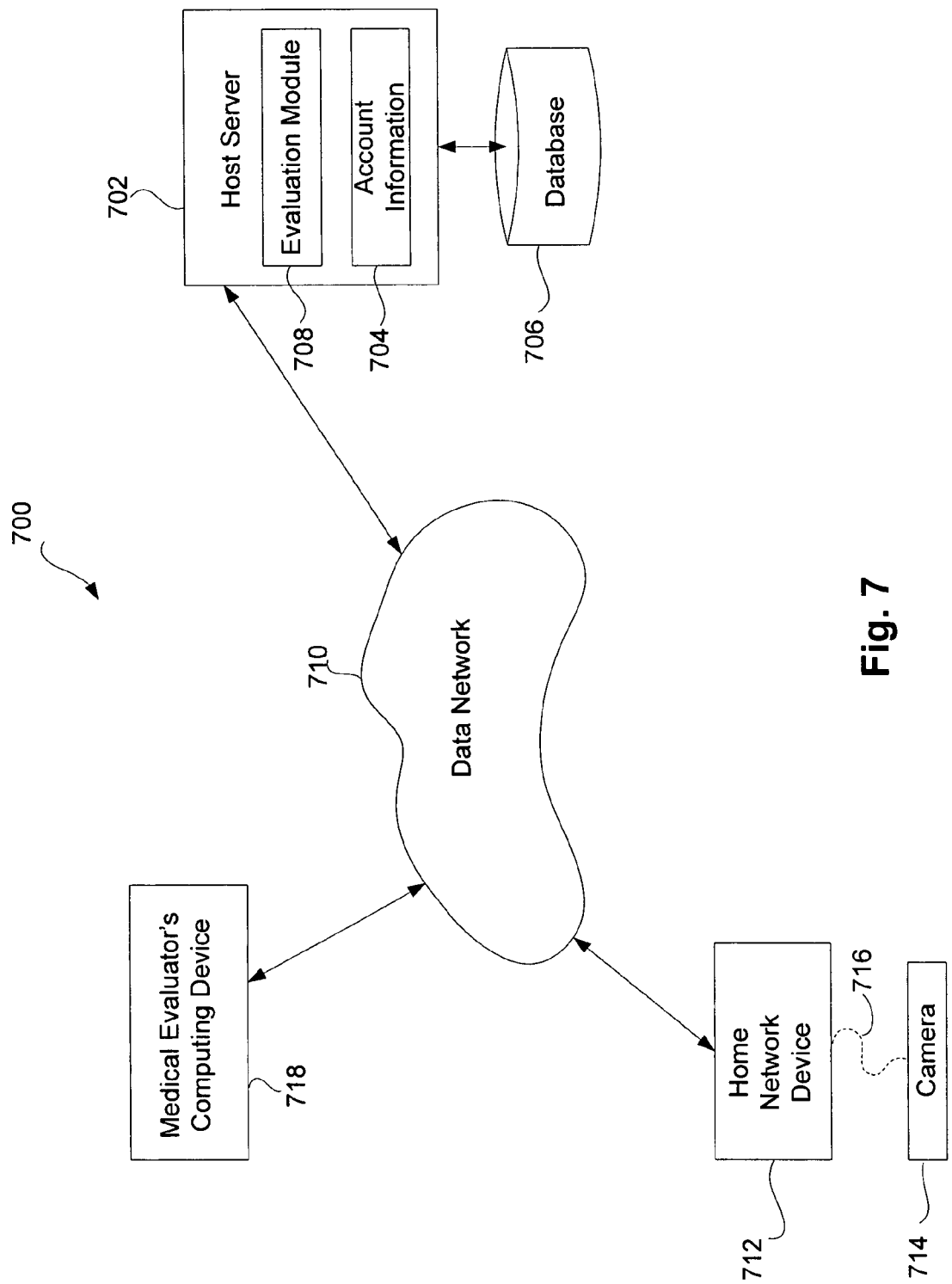
FIG. 7 is a distributed health and wellness system according to one embodiment of the invention.

FIG. 7 is a distributed health and wellness system 700 according to one embodiment of the invention. The distributed health and wellness system 700 includes a host server 702, which can be a networked computer. The host server 702 stores account information 704 corresponding to a plurality of registered end-users. The host server 702 maintains health and wellness data for the various end-users. The health and wellness data is typically stored in a database 706. The host server 702 can also process the health and wellness data using an evaluation module 708.

The host server 702 couples to a data network 710. The data network 710 can be a wide area or global area network. For a given end-user, a home network device 712 can couple to the data network 710. For example, the home network device 712 can be a personal computer or a personal health and wellness system for in-home or personal use. In one embodiment, the home network device 712 supports the capture of images pertaining to health and wellness of an end-user, and a camera 714 is utilized by the end-user. The end-user uses the camera 714 to capture images corresponding to health and wellness conditions of the end-user. In one approach, the camera 714 is capable of electrically coupling to the home network device 712 over a link 716. The link 716 can be a wireless link or a wired link or a connector established link.

In one embodiment, the distributed health and wellness system 700 can further permit medical evaluators to access the health and wellness data for the various end-users being stored by the host server 702. In this regard, the health and wellness data, such as the health and wellness images provided by the camera 714, can be uploaded by the home network device 712 through the data network 710 to the host server 702. The host server 702 can store the health and wellness images in the database 706 such that they are associated with the pertinent user account associated with the end-user. The host server 702 can also process the health and wellness data using the evaluation module 708. The evaluation module 708 can evaluate whether specific medical conditions exist based on a computerized examination of the health and wellness data. The evaluation module 708 can also determine whether a medical evaluation by a medical evaluator (or medical representative) should be performed using the health and wellness data associated with a particular end-user. When the host server 702, namely, the evaluation module 708, determines that a medical evaluator should review the health and wellness data for a particular end-user, the host server 702 can notify a medical evaluator's computing device 718 via the data network 710. The medical evaluator associated with the medical evaluator's computing device 718 can then access the health and wellness data for the particular end-user via the host server 702 and provide an evaluation of any existing health and wellness conditions that require attention. The medical evaluation or report can then be returned to the host server 702 via the data network 710. The report can also be stored in the database 706.

Figure 8A:
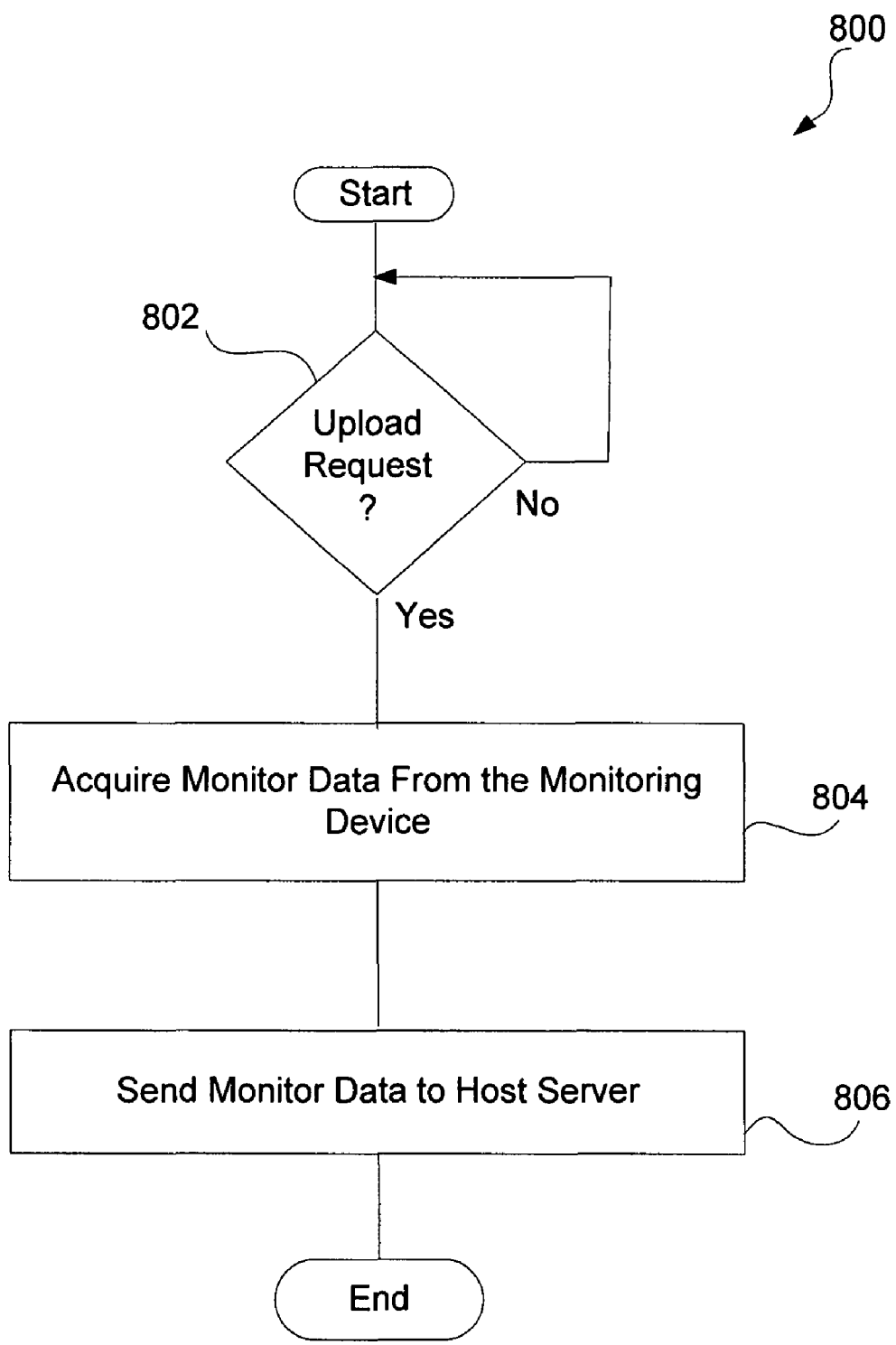
FIG. 8A is a flow diagram of a monitoring data upload process according to one embodiment of the invention.

FIG. 8A is a flow diagram of a monitoring data upload process 800 according to one embodiment of the invention. The monitoring data upload process 800 can, for example, be performed by the home network device 712 illustrated in FIG. 7. The monitoring data upload process 800 begins with a decision 802. The decision 802 determines whether an upload request has been received. An upload request can be provided by an end-user through a manual user action, or can be automatically initiated by the home network device 712, or can be requested by the host server 702. In any case, when the decision 802 determines that an upload request has not been received, then the monitoring data upload process 800 awaits such a request. Once the decision 802 determines that an upload request has been received, data, including monitoring data, from the monitoring device is acquired 804. The monitor data is then sent 806 to the host server. Typically, to secure the monitoring data, the monitor data would be encrypted prior to its transmission to the host server. Additionally, the home network device 712 could authenticate the camera 714 prior to transmission of the monitor data to the host server. The home network device 712 also could authenticate itself with the host server 702. The authentication of the camera 714 can ensure that the camera 714 is authorized for use with the host server 702. The authentication of the home network device 712 can ensure that the home network device 712 is authorized for use with the host server 702 and/or ensure that the user of the home network device 712 is an authorized (and registered) user of the system. After the monitor data has been sent to the host server, the monitoring data upload process 800 is complete and ends.

Figure 8B:
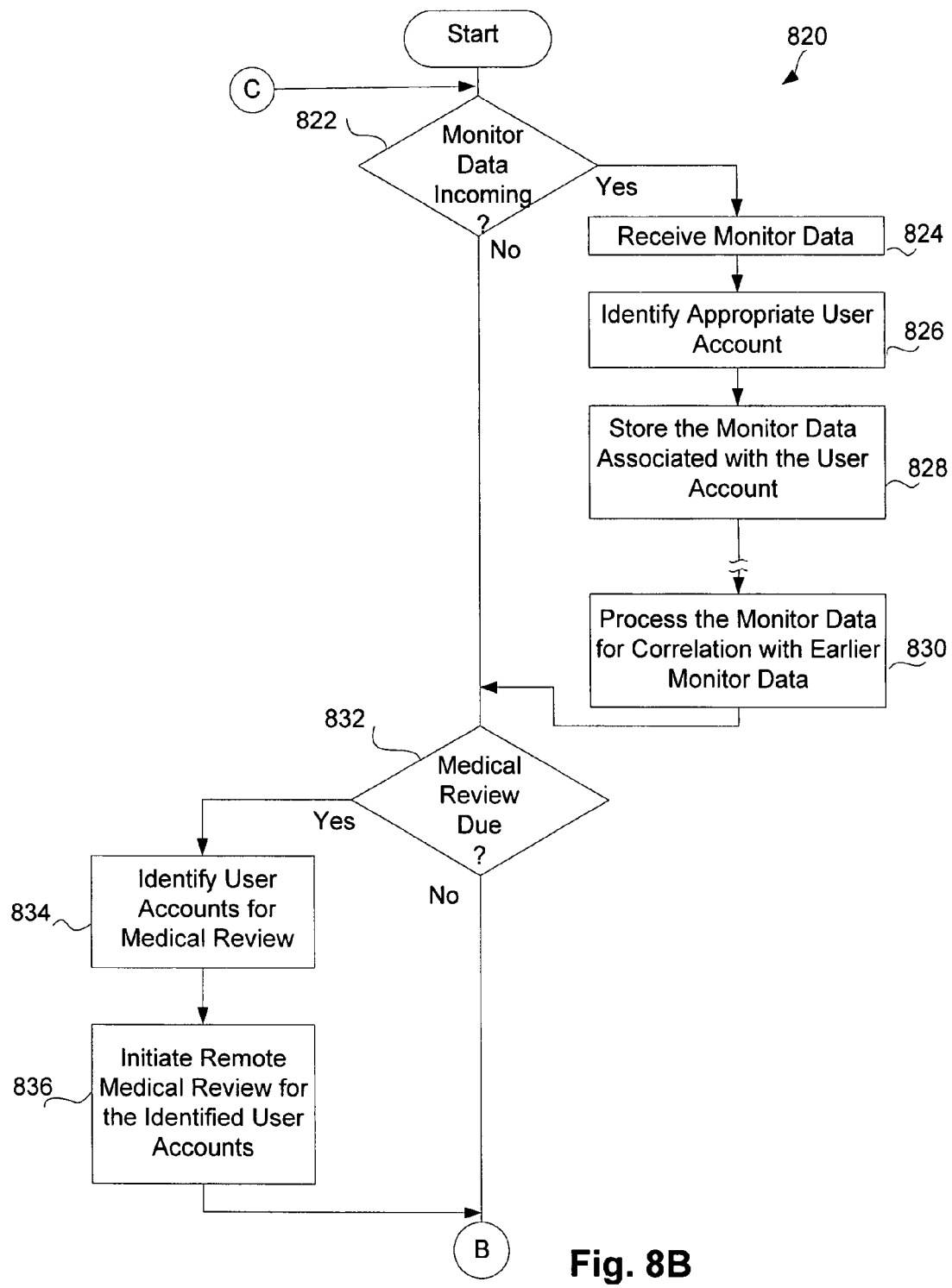
FIGS. 8B and 8C are flow diagrams of a host server process according to one embodiment of the invention.
Figure 8C:
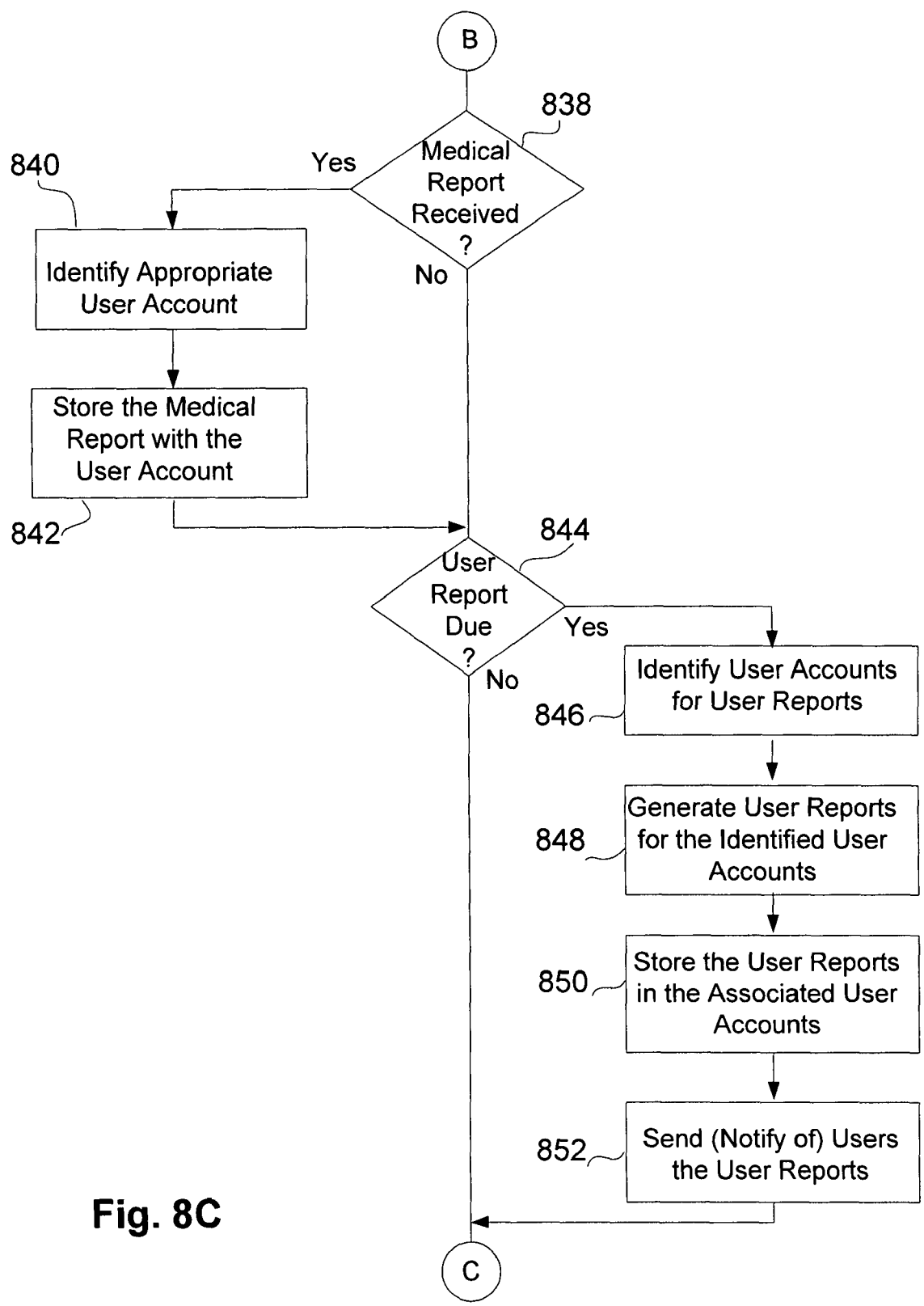

FIGS. 8B and 8C are flow diagrams of a host server process 820 according to one embodiment of the invention. For example, the host server process 820 can be performed by the host server 702 illustrated in FIG. 7.

The host server process 820 begins with a decision 822. The decision 822 determines whether monitor data is incoming. When the decision 822 determines that monitor data is incoming, the monitor data is received 824. In addition, an appropriate user account may be identified 826. If the monitor data is associated with a particular end-user, the identification 826 of the appropriate user account can be important. If the monitor data is associated with a particular end-user, next, the monitor data is stored 828 such that it is associated with the corresponding user account. Subsequently, although other processing may intervene, the monitor data can be processed 830 for correlation with earlier monitor data. The ability to correlate current monitor data with earlier monitor data can be advantageous when the monitor data is provided over an extended period of time and the evolution and change in the monitor dated is important for health and wellness evaluation.

Following the block 830, or directly following the decision 822 when the monitor data is not incoming, a decision 832 determines whether a medical review is due or appropriate. A medical review can be initiated by the host server 702. For example, the medical review could be periodically requested or could be requested when the evaluation module 708 indicates that irregularity (or certain particular features) exists in the monitor data. In any case, when the decision 832 determines that a medical review is due or appropriate, one or more user accounts for medical review are identified 834. Then, medical review or remote medical review for the identified user accounts is initiated 836.

Following the block 836, or directly following the decision 832 when a medical review is not due, a decision 838 determines whether a medical report has been received. When the decision 838 determines that a medical report has been received, an appropriate user account associated with the medical report is identified 840. Then, the medical report is stored 842 associated with the user account.

Following the block 842, or following the decision 838 directly when a medical report has not been received, a decision 844 determines whether a user report is due. When the decision 844 determines that a user report is due, a user account for one or more user reports are identified 846. User reports are then generated 848 for the identified user account. The user reports are then stored 850 in the associated user accounts. Thereafter, the user is sent (or notified of) 852 the user reports.

Following the block 852, or directly following the decision 844 when a user report is not due, the host server process 820 returns to repeat the decision 822 and subsequent blocks so that the host server process 820 can repeat and process other incoming data or requests.

Figure 9:
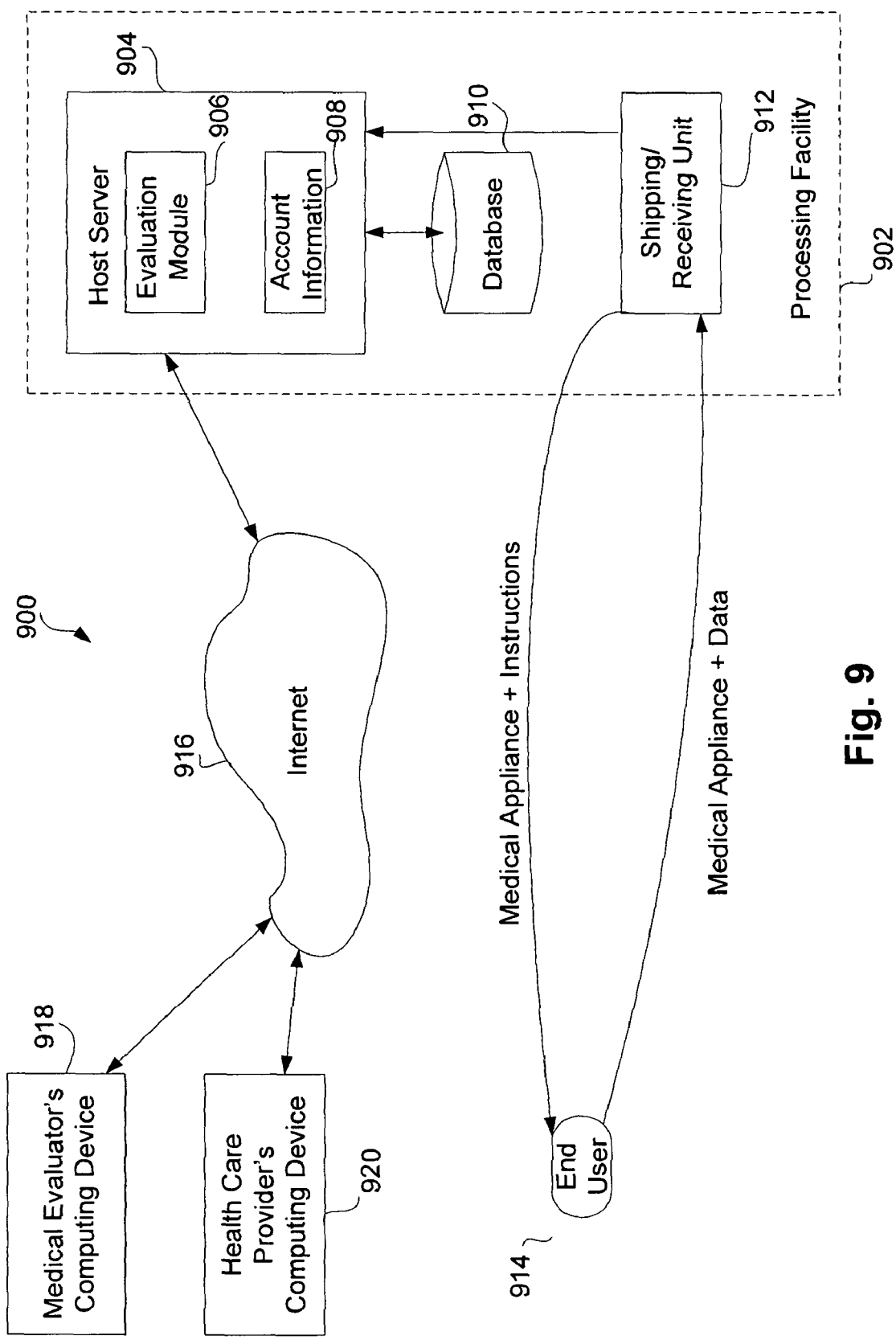
FIG. 9 is a distributed health and wellness system according to another embodiment of the invention.

FIG. 9 is a distributed health and wellness system 900 according to another embodiment of the invention. The distributed health and wellness system 900 includes a processing facility 902. The processing facility 902 includes a host server 904. The host server 904 is a computing device that controls overall operation of the processing facility 902. The host server 904 includes an evaluation module 906 and account information 908. Coupled to the host server 904 is a database 910. The database 910 can store health and wellness data corresponding to various end-users who have registered with the host server 904 and have account information stored in the account information area 908. The processing facility 902 also includes a shipping/receiving unit 912. The shipping/receiving unit 912 operates to send shipments to and receive shipments from a plurality of different end-users 914 and other facilities. In particular, the shipping/receiving unit 912 can ship a medical appliance together with usage instructions to an end-user 914. The instructions can inform the end-user 914 about how to use the medical appliance to acquire health and wellness data. After the end-user 914 has used the medical appliance, the end-user 914 can return all or a portion of the medical appliance together with the acquired health and wellness data back to the shipping/receiving unit 912 of the processing facility 902.

The shipping/receiving unit 912 can then acquire the health and wellness data for the end-user 914 from the returned materials, such as the returned medial appliance, and supplies such to the host server 904. The host server 904 associates the health and wellness data to the associated user and stores such health and wellness data in the database 910. The evaluation module 906 can then evaluate the health and wellness data within the database 910 to determine when a remote medical evaluation is to be performed by a medical person. When the evaluation module 906 indicates that a medical evaluation is appropriate, the host server 904 informs a medical evaluator's computing device 918, which can be a personal computer, PDA, or cell phone, via a network 916, such as the Internet, that an evaluation of certain health and wellness data is requested. The medical person associated with the medical evaluator's computing device 918 can then access the health and wellness data for the user of interest and perform an evaluation. The evaluation is then returned to the host server 904 via the network 916, and then stored in the database 910.

In some embodiments, the medical evaluation is done by a medical person that is capable of evaluating specific health and wellness data. For example, the medical person can be a specialist that specializes in reviewing images of skin conditions. In such case, the medical specialist can be very efficient in reviewing the health and wellness data for their specific field(s) of expertise. On the other hand, the medical person could be a more general practice type medical person, or could even be the health care provider for the end-user. In any case, the distributed health and wellness system 900 can also permit health care providers' computing devices access to the processing facility 902, namely, access the health and wellness data associated with end-users under their care. Hence, a health-care provider's computing device 920 can couple to the host server 904 via the Internet 916.

Figure 10A:
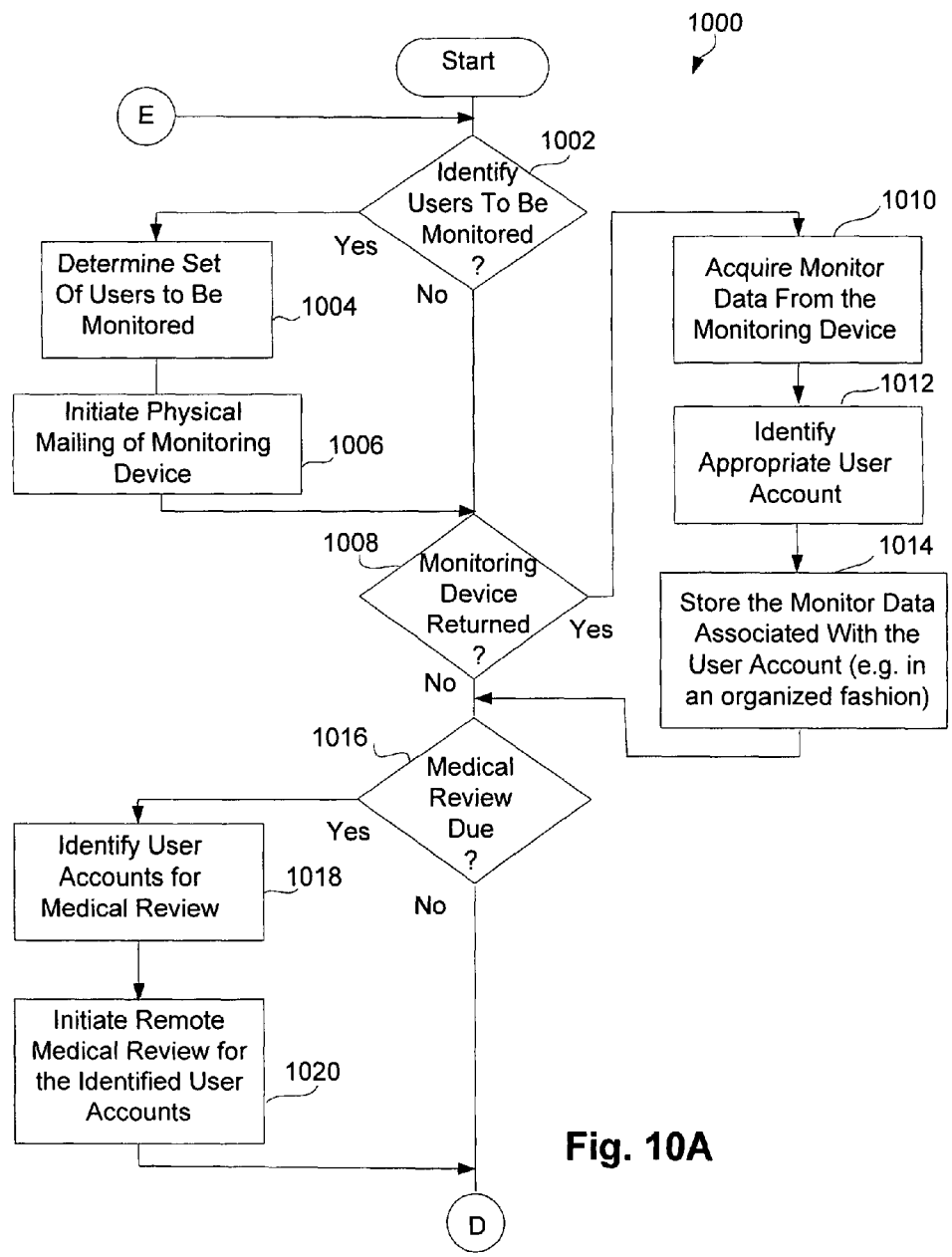
FIGS. 10A and 10B are flow diagrams of a server process according to one embodiment of the invention.
Figure 10B:
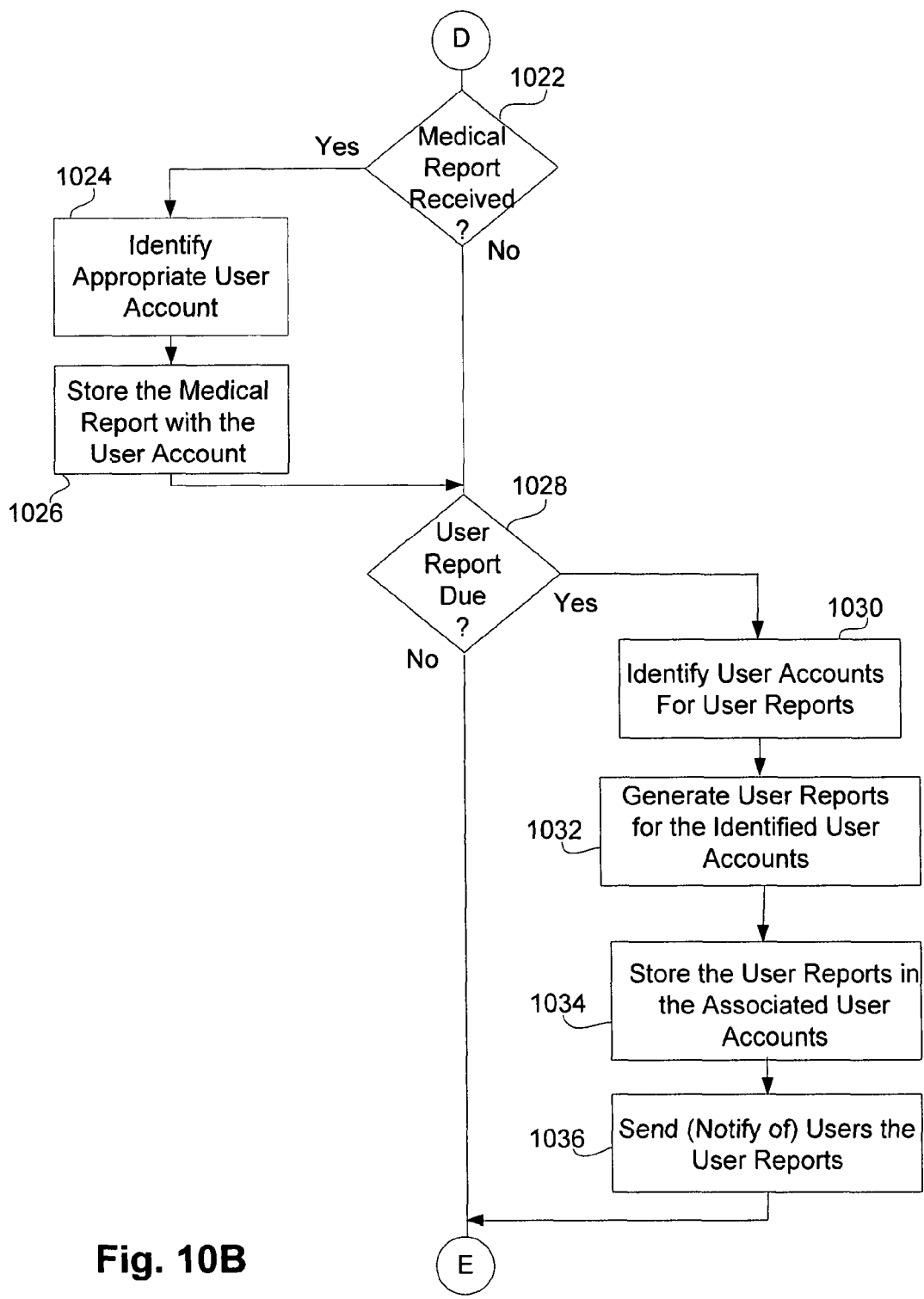

FIGS. 10A and 10B are flow diagrams of a server process 1000 according to one embodiment of the invention. The server process 1000 is, for example, performed by a host server, such as the host server 904 illustrated in FIG. 9.

The server process 1000 begins with a decision 1002 that determines whether one or more users to be monitored are to be identified. When the decision 1002 determines that a number of users to be monitored are to be identified, a set of users to be monitored is determined 1004. Then, physical mailing of monitoring devices is initiated 1006 to the set of users. The physical mailing can, for example, be performed or controlled by the shipping/receiving unit 912 illustrated in FIG. 9.

Following the block 1006, or directly following the decision 1002 when the decision 1002 determines that users to be monitored are not to be identified at this time, a decision 1008 determines whether a monitoring device has been returned. When the decision 1008 determines that a monitoring device has been returned, such as to the shipping/receiving unit 912, monitored data can be acquired 1010 from the returned monitoring device. An appropriate user account is identified 1012. The monitored data associated with the user account is then stored 1014. Normally, the monitored data would be stored such that it is organized with respect to previously stored data for the corresponding user. In other words, the data can be correlated with earlier data to provide organized storage. With the data stored in an organized manner, subsequent evaluation of the data can become more efficient and, for certain wellness data, more accurate.

Following the block 1014, or directly following the decision 1008 when the decision 1008 determines that a monitoring device has not been returned, a decision 1016 determines whether a medical review is due or appropriate. When the decision 1016 determines that a medical review is due, one or more user accounts for medical review are identified 1018. In one embodiment, medical review can be initiated periodically for each user, by a health care provider's request, by an end-user's request, and/or automatically by computerized evaluation of the stored monitored data. The medical review can be of different types, including different conditions, diseases, infections, etc. Then, remote medical review for the identified user accounts can be initiated 1020. Here, the server process 1000 can select from a variety of different medical evaluators such that the evaluator to be utilized is appropriate for the type of medical review desired. The medical evaluator that provides the remote medical review can complete a report for the evaluation he or she has performed.

Following the block 1020, or directly following the decision 1016 when a medical review is not due, a decision 1022 determines whether a medical report has been received. When the decision 1022 determines that a medical report has been received, an appropriate user account associated with the medical report is identified 1024. Then, the medical report is stored 1026 associated with the user account.

Following the block 1026, or following the decision 1022 directly when a medical report has not been received, a decision 1028 determines whether a user report is due. When the decision 1028 determines that a user report is due, one or more user accounts for one or more user reports are identified 1030. One or more user reports are then generated 1032 for the identified user accounts. The user reports can then be stored 1034 in the associated user accounts. Thereafter, one or more users are sent (or notified of) 1036 the user reports.

Following the block 1036, or directly following the decision 1028 when a user report is not due, the host server process 1000 returns to repeat the decision 1002 and subsequent blocks so that the host server process 1000 can repeat and process other incoming data or requests.

In still another embodiment of the invention, a distributed health and wellness system can provide a medical monitoring device or appliance at a retail or discount store. A customer, while visiting the store, can purchase the medical monitoring device or appliance. In one embodiment, the medical monitoring device or appliance can be provided within a kit that further includes one or more of a computer readable medium including computer program code for execution by a computer to assist the customer (user) in acquiring and transmitting health data to a remote facility, either physically or electronically, instruction for operation of the medical monitoring device or appliance, and/or possibly a cable for connecting the medical monitoring device or appliance to a host device (e.g., computer) server.

The medical monitoring device or appliance can monitor various different health or wellness conditions of a user. As an example, the medical monitoring device or appliance can monitor skin or other conditions, chemical analysis for bodily fluids, etc. The medical monitoring device or appliance can, for example, be a probe, a container, or sensor. The medical monitoring device or appliance can use one or more of a reagent, an electrical component, an electrical circuit, and data storage.

Figure 11:
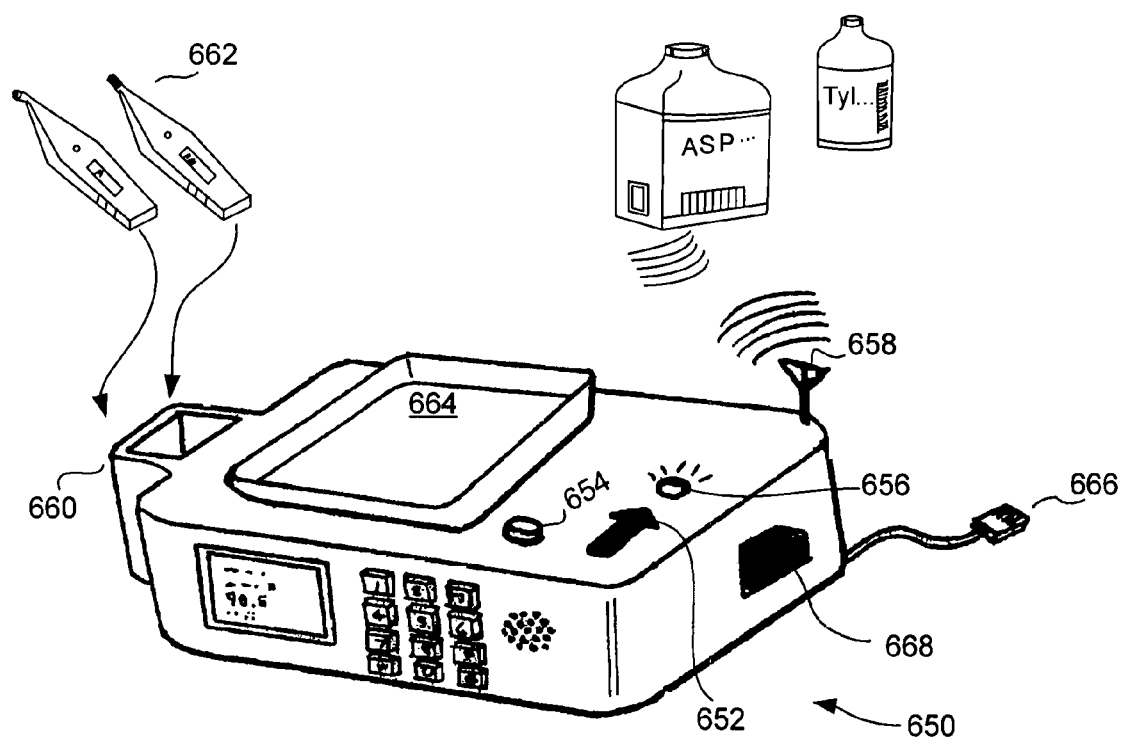
FIG. 11 shows one embodiment of such a base that can be electrically coupled to a medical monitoring device or appliance.

In one embodiment, any of a number of functions previously described as being performed by a medical monitoring device or appliance can be performed by a base. FIG. 11 shows one embodiment of such a base 650 that can be electrically coupled to a medical monitoring device or appliance.

In one embodiment, in such a base implementation, operations performed by a medical monitoring device can be minimized. For example, when the user gets his medication from a pharmacist, the device, such as a bottle, can include information regarding the prescription, which can include the user's schedule to take the medication. Such information can be on a barcode, a RFID tag or in a memory in the device, according to different embodiments. The user can facilitate downloading such information from the device into the base 650. For example, if the information is in a barcode on a device, the base 650 can include a barcode reader 652. The user can push a start button 654, and then the user can scan the barcode to enter such information into the base 650. When the barcode is successfully scanned, a signal can be provided to the user, such as a light 656 can turn on, or an audio feedback can be provided by a speaker. Note that different pharmacies might use different barcodes. In one embodiment, information regarding different barcodes from the different pharmacies is stored in the base 650. In one embodiment, the base 650 can include a RFID tag reader, including its antenna 658, to access the information stored in an RFID tag.

Alternatively, the device or appliance can include an electrical connector. The user can connect the device's connector to a base connector at the base 650 to download the information. In one embodiment, the device's connector is located at the bottom of the device. There can be a recessed space on top of the base 650 to receive the device. When the user puts the device into the space, with the device's connector received by the base's connector, information in the device can be downloaded into the base. In one embodiment, the device's connector can be at the bottom of the device. The device's connector can be a standard connector, such as a USB connector. The connector can be slightly recessed into the device, allowing the device to firmly stand on a flat surface, without the connector sticking out.

In one embodiment, the base 650 includes a slot 660 to receive a sensor 662, such as a thermometer. The slot 660 can be used to track different measurements regarding an end-user. Each time a sensor is stationed in the space, such as inserted into the slot 660, measurements made by the sensor 662, such as in the past 24 hours, are uploaded to the base 650. The upload can be through a connector at the sensor 662 with a corresponding connector at the base 650. The sensor 662 is one example of a medical monitoring device or appliance that can be used with the base 650.

In one embodiment, the base 650 can also include a scale 664. An end-user can weigh a device with the scale 664. The scale 664 can also be at a recessed space on top of the base 650 to receive the device. In another embodiment, as the device sits on the scale 664, its RFID tag is read by a RFID tag reader in the base 650.

In another embodiment, the base can have multiple recessed spaces for more than one device. The base can also have multiple slots for more than one sensor to be stationed.

In another embodiment, the base 650 can include a connector 666 to connect to other devices or instruments, such as a computer. Instead of a physical connector, the connection can also be wireless. Based on such connections, the base 650 can be connected, for example, to another area, such as a website. Information in the base 650 can be accessed and the base 650 can also access information from the another area, such as the website. In yet another embodiment, the base 650 can also include another input/output connector 668, which can be for a memory device, such as a flash memory card.

In one embodiment, the base 650 can keep track of the time, the date, the weight of a medical monitoring device, sensor measurements from a medical monitoring device and/or the identity of the end-user using the base 650 and/or medical monitoring device. In one embodiment, the device can contain medication. For example, the device can be a bottle of pill. Every time the end user uses the device, the user can place the device on a selected space on the base 650 to weigh the device and to download information into the base 650. This would allow the base 650 to keep track of information related to the user taking the medication.

In one embodiment, since the device can keep track of the type of substance taken by the user, as the user takes different types of substances, such as from different devices, the information regarding the substance can be downloaded into the base 650 accordingly. Based on information in the base 650, or information accessed from a remote site or area, the base can provide indication to the user that the different types of medication the user is taking, conflict with each other and can cause complications to the user.

In one embodiment, a base 650 is, or performs the functions of, a medical monitoring system. In another embodiment, a base 650 can be considered personal to an end-user in the sense that the user typically does not want to share it with another end-user if the another person is using the base 650 for similar purposes as the user. This can be similar to a toothbrush, which is usually considered personal to the user. However, the user may be willing to let a healthcare provider use it because the provider is typically using the base 650 for different purposes, such as to access information from it to diagnose the user.

Different processes have been described regarding analyzing and processing images captured. In one embodiment, the analysis includes color analysis. For example, the colors of optical images of lesions can be analyzed to provide additional skin condition information.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

Certain aspects of the invention can be implemented in software, hardware or a combination of hardware and software. Certain aspects of the invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield one or more of the following advantages. One potential advantage of the invention is that health care costs can be significantly lowered. Another potential advantage of the invention is that through use of technology associated with the invention quality health care can be provided in the privacy and convenience of one's home. More people may be interested in checking themselves more often and more regularly, given it ease of use and given that the user's portion of the testing can be done in the privacy of the user's home. Still another potential advantage of the invention is that a health and wellness system as described herein can provide standardized, consistent health and wellness data that can be used by hospitals, medical researchers, doctors, and end-users.

Numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

In the foregoing description, reference to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

The many features and advantages of the present invention are apparent from the written description. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A health care monitoring system, comprising:
   a data management subsystem that at least coordinates storage and retrieval of medical information for a plurality of users;
   a remote medical review subsystem that at least coordinates review of one or more of the users' stored medical information available from said data management subsystem;
   a health care provider subsystem including at least one computer configured to at least permit authorized health care providers to access stored medical information available from said data management subsystem; and
   a monitoring device delivery/return subsystem that at least coordinates the delivery and/or return of monitoring devices configured for at least monitoring certain health conditions of a plurality of the users,
   wherein information regarding the certain health conditions monitored by the monitoring devices is subsequently stored in the data management subsystem,
   wherein said health care monitoring system determines when a particular type of health monitoring is to be performed by one or more of the plurality of users at a specific time,
   wherein said monitoring device delivery/return subsystem coordinates sending a monitoring device corresponding to the particular type of health monitoring to the one or more of the plurality of users, and
   wherein the particular type of health monitoring includes skin condition monitoring, and the monitoring device is configured to participate in skin condition monitoring.

2. A health care monitoring system as recited in claim 1, wherein when the particular type of health monitoring is skin condition monitoring, the monitoring device includes at least a heating mechanism and a thermal image acquisition mechanism.

3. A health care monitoring system as recited in claim 1, wherein when the particular type of health monitoring is skin condition monitoring, the monitoring device includes at least a camera box.

4. A health care monitoring system as recited in claim 1, wherein the type of health monitoring is designed to be performed by the one or more of the plurality of users at home.

5. A health care monitoring system as recited in claim 1, wherein said health care provider subsystem limits access to the stored medical information to authorized individual or by way of a group affiliation.

6. A health care monitoring system as recited in claim 1, wherein the monitoring device includes at least an image acquisition device.

7. A health care monitoring system as recited in claim 6, wherein the image acquisition device is provided to assist the one or more of the plurality of users in capturing pictures of skin conditions of the one or more of the plurality of users.

8. A health care monitoring system as recited in claim 7, wherein the image acquisition device comprises a camera and a housing, and
wherein the housing includes at least:
- a camera interface suitable for being coupled to a camera, the camera interface including an opening to allow images to be captured by the camera; and
- a skin surface interface suitable for being coupled to a skin surface of the user, the skin surface interface including an opening that provides a picture border for the pictures being taken.

9. A health care monitoring system as recited in claim 8, wherein the camera interface enables the camera to be removably coupled thereto.

10. A health care monitoring system as recited in claim 8, wherein an inner surface of the skin surface interface includes at least a portion of a ruler.

11. A health care monitoring system as recited in claim 8, wherein the housing further includes a lens, the lens being provided internal to the housing and positioned between the camera interface and the skin surface interface, and at a predetermined distance from the skin surface interface.

12. A health care monitoring system as recited in claim 11, wherein the lens is movable to provide two predetermined distances from the skin surface interface, with a first distance being for close-up pictures, and a second distance being for taking pictures further away.

13. A health care monitoring system as recited in claim 12, wherein the camera or the housing further includes a light for use in providing light when pictures are taken.

14. A health care monitoring system as recited in claim 8, wherein the camera is a disposable digital camera.

15. A health care monitoring system, comprising:
- a data management subsystem that at least coordinates storage and retrieval of medical information for a plurality of users;
- a health care provider subsystem including at least one computer configured to at least permit authorized health care providers to access stored medical information available from said data management subsystem; and
- a monitoring device delivery/return subsystem that at least coordinates the delivery and/or return of monitoring devices configured for at least monitoring certain health conditions of a plurality of the users,
- wherein information regarding the certain health conditions monitored by the monitoring devices is subsequently stored in the data management subsystem,
- wherein said health care monitoring system is configured to determine when a particular type of health monitoring is to be performed by one or more of the plurality of users using a particular monitoring device corresponding to the particular type of health monitoring,
- wherein said monitoring device delivery/return subsystem is configured to coordinate sending the particular monitoring device to the one or more of the plurality of users, and
- wherein the particular type of health monitoring includes skin condition monitoring, and the monitoring device is configured to participate in skin condition monitoring.

16. A health care monitoring system as recited in claim 15, wherein the type of health monitoring is designed to be performed by the one or more of the plurality of users at home.

17. A health care monitoring system as recited in claim 15, wherein said health care provider subsystem limits access to the stored medical information to authorized individual or by way of a group affiliation.

18. A health care monitoring system as recited in claim 15, wherein the particular monitoring device includes at least an image acquisition device.

19. A health care monitoring system as recited in claim 18, wherein the image acquisition device is provided to assist the one or more of the plurality of users in capturing pictures of skin conditions of the one or more of the plurality of users.

20. A health care monitoring system as recited in claim 19, wherein the image acquisition device comprises a camera and a housing, and
wherein the housing includes at least:
- a camera interface suitable for being coupled to a camera, the camera interface including an opening to allow images to be captured by the camera; and
- a skin surface interface suitable for being coupled to a skin surface of the user, the skin surface interface including an opening that provides a picture border for the pictures being taken.

21. A health care monitoring system as recited in claim 20, wherein the camera interface enables the camera to be removably coupled thereto.

22. A health care monitoring system as recited in claim 20, wherein the housing further includes a lens, the lens being provided internal to the housing and positioned between the camera interface and the skin surface interface, and at a predetermined distance from the skin surface interface, and
wherein the lens is movable to provide at least two predetermined distances from the skin surface interface, with a first distance being for close-up pictures, and a second distance being for taking pictures further away.

23. A health care monitoring system as recited in claim 20, wherein the camera is a disposable digital camera.

\* \* \* \* \*